US009622922B2

(12) United States Patent
Nelson

(10) Patent No.: US 9,622,922 B2
(45) Date of Patent: Apr. 18, 2017

(54) STRETCH BREATHABLE PROTECTIVE ABSORBENT ARTICLE USING BILAMINATE

(71) Applicant: Medline Industries, Inc., Mundelein, IL (US)

(72) Inventor: Christopher Nelson, Hiram, GA (US)

(73) Assignee: Medline Industries, Inc., Mundelein, IL (US)

( * ) Notice: Subject to any disclaimer, the term of this patent is extended or adjusted under 35 U.S.C. 154(b) by 14 days.

(21) Appl. No.: 14/306,325

(22) Filed: Jun. 17, 2014

(65) Prior Publication Data

US 2015/0297423 A1 Oct. 22, 2015

Related U.S. Application Data

(63) Continuation-in-part of application No. 14/257,481, filed on Apr. 21, 2014.

(51) Int. Cl.
*A61F 13/15* (2006.01)
*A61F 13/20* (2006.01)
(Continued)

(52) U.S. Cl.
CPC .... *A61F 13/51478* (2013.01); *A61F 13/4902* (2013.01); *A61F 13/49061* (2013.01);
(Continued)

(58) Field of Classification Search
CPC .......... A61F 13/49007; A61F 13/49009; A61F 13/49011; A61F 2013/49007; A61F 2013/49009; A61F 2013/49036
(Continued)

(56) References Cited

U.S. PATENT DOCUMENTS 688,143 A 12/1901 Windle
1,614,239 A 1/1927 Hammond
(Continued)

FOREIGN PATENT DOCUMENTS

WO 0037005 A2 6/2000
WO 2006017718 A1 2/2006
(Continued)

OTHER PUBLICATIONS

Notification of Transmittal of the International Search Report and the Written Opinion of the International Searching Authority, or the Declaration; International Application No. PCT/US2015/026119; Medline Industries, Inc. (Nelson), Jul. 1, 2015.
(Continued)

*Primary Examiner* — Michele M Kidwell
(74) *Attorney, Agent, or Firm* — Laubscher, Spendlove & Laubscher, P.C.

(57) ABSTRACT

A disposable absorbent article of a brief or pull-up type incorporates a breathable laminate material composed of two layers. The laminate is an elastic material and may include non-elastic portions created by deactivating the material. The laminate material may be made breathable by the ultrasonic bonding process used to create the laminate. A third layer is adhered or bonded to the laminate and with leg elastics positioned between the laminate that the third layer. The absorbent article includes an absorbent assembly that overlaps with the non-elastic portions of the laminate.

17 Claims, 10 Drawing Sheets

(51) Int. Cl.
*A61F 13/514* (2006.01)
*A61F 13/49* (2006.01)

(52) U.S. Cl.
CPC .. *A61F 13/51458* (2013.01); *A61F 13/51464* (2013.01); *A61F 2013/49022* (2013.01)

(58) Field of Classification Search
USPC ........................................ 604/385.24, 385.27
See application file for complete search history.

(56) References Cited

U.S. PATENT DOCUMENTS

| | | |
|---|---|---|
| RE26,151 E | 1/1967 | Duncan et al. |
| 3,338,992 A | 8/1967 | Kinney |
| 3,341,394 A | 9/1967 | Kinney |
| 3,485,706 A | 12/1969 | Evans |
| 3,502,538 A | 3/1970 | Petersen |
| 3,502,763 A | 3/1970 | Hartmann |
| 3,542,615 A | 11/1970 | Dobo et al. |
| 3,612,055 A | 10/1971 | Mesek et al. |
| 3,692,618 A | 9/1972 | Carduck et al. |
| 3,802,817 A | 4/1974 | Matsuki et al. |
| 3,849,241 A | 11/1974 | Harding et al. |
| 3,860,003 A | 1/1975 | Buell |
| 3,955,575 A | 5/1976 | Okuda |
| 3,994,486 A | 11/1976 | Nystrand |
| 4,050,462 A | 9/1977 | Woon et al. |
| 4,051,853 A | 10/1977 | Egan, Jr. |
| 4,055,180 A | 10/1977 | Karami |
| 4,084,592 A | 4/1978 | Tritsch |
| 4,145,763 A | 3/1979 | Abrams et al. |
| 4,195,634 A | 4/1980 | DiSalvo et al. |
| 4,205,679 A | 6/1980 | Repke et al. |
| 4,246,900 A | 1/1981 | Schroder |
| 4,251,643 A | 2/1981 | Harada et al. |
| 4,253,461 A | 3/1981 | Strickland et al. |
| 4,296,750 A | 10/1981 | Woon et al. |
| 4,317,449 A | 3/1982 | Novakoski |
| 4,340,563 A | 7/1982 | Appel et al. |
| 4,381,781 A | 5/1983 | Sciaraffa et al. |
| 4,402,690 A | 9/1983 | Redfern |
| 4,410,324 A | 10/1983 | Sabee |
| 4,413,996 A | 11/1983 | Taylor |
| 4,500,316 A | 2/1985 | Damico |
| 4,516,976 A | 5/1985 | Bell |
| 4,560,381 A | 12/1985 | Southwell |
| 4,596,568 A | 6/1986 | Flug |
| 4,610,680 A | 9/1986 | LaFleur |
| 4,610,682 A | 9/1986 | Kopp |
| 4,615,695 A | 10/1986 | Cooper |
| 4,639,254 A | 1/1987 | LeGault et al. |
| 4,643,932 A | 2/1987 | Daniels |
| 4,662,875 A | 5/1987 | Hirotsu et al. |
| 4,663,220 A | 5/1987 | Wisneski et al. |
| 4,670,012 A | 6/1987 | Johnson |
| 4,673,402 A | 6/1987 | Weisman et al. |
| 4,680,012 A | 7/1987 | Morley et al. |
| 4,695,278 A | 9/1987 | Lawson |
| 4,699,620 A | 10/1987 | Bernardin |
| 4,699,622 A | 10/1987 | Toussant et al. |
| 4,704,116 A | 11/1987 | Enloe |
| 4,705,513 A | 11/1987 | Sheldon et al. |
| 4,710,190 A | 12/1987 | Wood et al. |
| 4,720,415 A | 1/1988 | Vander Wielen et al. |
| 4,753,649 A | 6/1988 | Pazdernik |
| 4,758,241 A | 7/1988 | Papajohn |
| 4,770,656 A | 9/1988 | Proxmire et al. |
| 4,798,603 A | 1/1989 | Meyer et al. |
| 4,834,735 A | 5/1989 | Alemany et al. |
| 4,838,885 A | 6/1989 | Bernardin |
| 4,842,596 A | 6/1989 | Kielpikowski et al. |
| 4,846,815 A | 7/1989 | Scripps |
| 4,869,724 A | 9/1989 | Scripps |
| 4,883,480 A | 11/1989 | Huffman et al. |
| 4,884,323 A | 12/1989 | Provost et al. |
| 4,911,702 A | 3/1990 | O'Leary et al. |
| 4,916,005 A | 4/1990 | Lippert et al. |
| 4,936,840 A | 6/1990 | Proxmire |
| 4,938,753 A | 7/1990 | Van Gompel et al. |
| 4,938,757 A | 7/1990 | Van Gompel et al. |
| 4,940,464 A | 7/1990 | Van Gompel et al. |
| 4,963,140 A | 10/1990 | Robertson et al. |
| 4,964,860 A | 10/1990 | Gipson et al. |
| 4,988,344 A | 1/1991 | Reising et al. |
| 4,988,345 A | 1/1991 | Reising et al. |
| 5,013,382 A | 5/1991 | Nalowaniec et al. |
| 5,019,063 A | 5/1991 | Marsan et al. |
| 5,019,072 A | 5/1991 | Polski |
| 5,019,073 A | 5/1991 | Roessler et al. |
| 5,024,672 A | 6/1991 | Widlund |
| 5,026,446 A | 6/1991 | Johnston et al. |
| 5,034,008 A | 7/1991 | Breitkopf |
| 5,046,272 A | 9/1991 | Vogt et al. |
| 5,047,023 A | 9/1991 | Berg |
| 5,055,103 A | 10/1991 | Nomura et al. |
| 5,061,259 A | 10/1991 | Goldman et al. |
| 5,061,262 A | 10/1991 | Chen et al. |
| 5,062,838 A | 11/1991 | Nalowaniec et al. |
| 5,069,678 A | 12/1991 | Yamamoto et al. |
| 5,087,253 A | 2/1992 | Cooper |
| 5,104,116 A | 4/1992 | Pohjola |
| 5,106,385 A | 4/1992 | Allen et al. |
| 5,108,384 A | 4/1992 | Goulait |
| 5,128,193 A | 7/1992 | Anapol et al. |
| 5,133,707 A | 7/1992 | Rogers et al. |
| 5,134,007 A | 7/1992 | Reising et al. |
| 5,147,343 A | 9/1992 | Kellenberger |
| 5,147,347 A | 9/1992 | Huang |
| 5,149,334 A | 9/1992 | Lahman et al. |
| 5,149,335 A | 9/1992 | Kellenberger et al. |
| 5,151,092 A | 9/1992 | Buell et al. |
| 5,156,793 A | 10/1992 | Buell et al. |
| 5,156,902 A | 10/1992 | Pieper et al. |
| 5,163,932 A | 11/1992 | Nomura et al. |
| 5,176,668 A | 1/1993 | Bernardin |
| 5,176,670 A | 1/1993 | Roessler et al. |
| 5,176,671 A | 1/1993 | Roessler et al. |
| 5,188,624 A | 2/1993 | Young, Sr. et al. |
| 5,188,627 A | 2/1993 | Igaue et al. |
| 5,192,506 A | 3/1993 | Kureshy et al. |
| 5,219,646 A | 6/1993 | Gallagher et al. |
| 5,224,405 A | 7/1993 | Pohjola |
| 5,226,992 A | 7/1993 | Morman |
| 5,234,422 A | 8/1993 | Sneller et al. |
| 5,235,515 A | 8/1993 | Ungpiyakul et al. |
| 5,236,429 A | 8/1993 | Widlund |
| 5,242,436 A | 9/1993 | Weil et al. |
| 5,246,433 A | 9/1993 | Hasse et al. |
| 5,248,309 A | 9/1993 | Serbiak et al. |
| 5,263,949 A | 11/1993 | Karami et al. |
| 5,275,588 A | 1/1994 | Matsumoto et al. |
| 5,275,590 A | 1/1994 | Huffman et al. |
| 5,279,604 A | 1/1994 | Robertson et al. |
| 5,286,543 A | 2/1994 | Ungpiyakul et al. |
| 5,288,546 A | 2/1994 | Roessler et al. |
| 5,294,478 A | 3/1994 | Wanek et al. |
| 5,295,988 A | 3/1994 | Muckenfuhs et al. |
| 5,300,057 A | 4/1994 | Miller et al. |
| 5,304,161 A | 4/1994 | Noel et al. |
| 5,304,162 A | 4/1994 | Kuen |
| 5,318,555 A | 6/1994 | Siebers et al. |
| 5,320,531 A | 6/1994 | Delizo-Madamba |
| 5,326,612 A | 7/1994 | Goulait |
| 5,330,458 A | 7/1994 | Buell et al. |
| 5,344,691 A | 9/1994 | Hanschen et al. |
| 5,348,547 A | 9/1994 | Payne et al. |
| 5,350,370 A | 9/1994 | Jackson et al. |
| 5,358,500 A | 10/1994 | Lavon |
| 5,364,382 A | 11/1994 | Latimer et al. |
| 5,370,634 A | 12/1994 | Ando et al. |
| 5,370,639 A | 12/1994 | Widlund |
| 5,383,872 A | 1/1995 | Roessler et al. |
| 5,387,208 A | 2/1995 | Ashton et al. |
| 5,399,219 A | 3/1995 | Roessler et al. |

(56) References Cited

U.S. PATENT DOCUMENTS

| | | |
|---|---|---|
| 5,403,302 A | 4/1995 | Roessier et al. |
| 5,411,497 A | 5/1995 | Tanzer et al. |
| 5,422,172 A | 6/1995 | Wu |
| 5,423,789 A | 6/1995 | Kuen |
| 5,425,377 A | 6/1995 | Caillouette |
| 5,425,725 A | 6/1995 | Tanzer et al. |
| 5,433,715 A | 7/1995 | Tanzer et al. |
| 5,439,458 A | 8/1995 | Noel et al. |
| 5,458,592 A | 10/1995 | Abuto et al. |
| 5,460,622 A | 10/1995 | Dragoo et al. |
| 5,462,541 A | 10/1995 | Bruemmer et al. |
| 5,466,513 A | 11/1995 | Wanek et al. |
| 5,468,236 A | 11/1995 | Everhart et al. |
| 5,486,167 A | 1/1996 | Dragoo et al. |
| 5,489,282 A | 2/1996 | Zehner et al. |
| 5,490,846 A | 2/1996 | Ellis et al. |
| 5,496,298 A | 3/1996 | Kuepper et al. |
| 5,496,428 A | 3/1996 | Sageser et al. |
| 5,501,679 A | 3/1996 | Krueger et al. |
| 5,507,895 A | 4/1996 | Suekane |
| 5,509,914 A | 4/1996 | Osborn, III |
| 5,509,915 A | 4/1996 | Hanson et al. |
| 5,527,300 A | 6/1996 | Sauer |
| 5,527,302 A | 6/1996 | Endres et al. |
| 5,527,304 A | 6/1996 | Buell et al. |
| 5,527,305 A | 6/1996 | Goulait et al. |
| 5,537,722 A | 7/1996 | Niederhofer et al. |
| 5,540,796 A | 7/1996 | Fries |
| 5,549,591 A | 8/1996 | Landvogt |
| 5,549,592 A | 8/1996 | Fries et al. |
| 5,554,243 A | 9/1996 | Igaue et al. |
| 5,556,394 A | 9/1996 | Roe et al. |
| 5,560,798 A | 10/1996 | Brusky |
| 5,562,646 A | 10/1996 | Goldman et al. |
| 5,562,650 A | 10/1996 | Everett et al. |
| 5,569,229 A | 10/1996 | Rogers |
| 5,571,096 A | 11/1996 | Dobrin et al. |
| 5,575,782 A | 11/1996 | Hasse et al. |
| 5,591,151 A | 1/1997 | Hasse et al. |
| 5,593,399 A | 1/1997 | Tanzer et al. |
| 5,595,567 A | 1/1997 | King et al. |
| 5,595,618 A | 1/1997 | Fries et al. |
| 5,599,335 A | 2/1997 | Goldman et al. |
| 5,599,620 A | 2/1997 | Huskey |
| 5,601,542 A | 2/1997 | Melius et al. |
| 5,603,707 A | 2/1997 | Trombetta et al. |
| 5,605,735 A | 2/1997 | Zehner et al. |
| 5,624,423 A | 4/1997 | Anjur et al. |
| 5,624,428 A | 4/1997 | Sauer |
| 5,624,429 A | 4/1997 | Long et al. |
| 5,628,741 A | 5/1997 | Buell et al. |
| 5,629,063 A | 5/1997 | Gobran |
| 5,634,917 A | 6/1997 | Fujioka et al. |
| 5,647,864 A | 7/1997 | Allen et al. |
| 5,659,538 A | 8/1997 | Stuebe et al. |
| 5,660,666 A | 8/1997 | Dilnik et al. |
| 5,669,894 A | 9/1997 | Goldman et al. |
| 5,669,900 A | 9/1997 | Bullwinkel et al. |
| 5,674,216 A | 10/1997 | Buell et al. |
| 5,681,300 A | 10/1997 | Ahr et al. |
| 5,683,533 A | 11/1997 | Keighley et al. |
| 5,683,794 A | 11/1997 | Wadsworth et al. |
| 5,685,873 A | 11/1997 | Bruemmer et al. |
| 5,690,628 A | 11/1997 | Huskey et al. |
| 5,706,524 A | 1/1998 | Herrin et al. |
| 5,718,698 A | 2/1998 | Dobrin et al. |
| 5,722,127 A | 3/1998 | Coates |
| 5,735,839 A | 4/1998 | Kawaguchi et al. |
| 5,735,840 A | 4/1998 | Kline et al. |
| 5,738,669 A | 4/1998 | Suzuki et al. |
| 5,741,241 A | 4/1998 | Guidotti et al. |
| 5,745,922 A | 5/1998 | Rajala et al. |
| 5,746,731 A | 5/1998 | Hisada |
| 5,749,865 A | 5/1998 | Yamamoto et al. |
| 5,749,866 A | 5/1998 | Roe et al. |
| 5,760,080 A | 6/1998 | Wada et al. |
| 5,769,838 A | 6/1998 | Buell et al. |
| 5,772,649 A | 6/1998 | Siudzinski |
| 5,779,831 A | 7/1998 | Schmitz |
| 5,785,699 A | 7/1998 | Schmitz |
| 5,795,350 A | 8/1998 | Schmitz |
| 5,797,893 A | 8/1998 | Wada et al. |
| 5,817,400 A | 10/1998 | Chen et al. |
| 5,820,617 A | 10/1998 | Igaue et al. |
| 5,830,206 A | 11/1998 | Larsson |
| 5,843,056 A | 12/1998 | Good et al. |
| 5,843,066 A | 12/1998 | Dobrin |
| 5,843,067 A | 12/1998 | Trombetta et al. |
| 5,843,575 A | 12/1998 | Wang et al. |
| 5,849,000 A | 12/1998 | Anjur et al. |
| 5,853,402 A | 12/1998 | Faulks et al. |
| 5,855,574 A | 1/1999 | Kling et al. |
| 5,858,515 A | 1/1999 | Stokes et al. |
| 5,858,535 A | 1/1999 | Wang et al. |
| 5,860,964 A | 1/1999 | Willekens et al. |
| 5,861,074 A | 1/1999 | Wu |
| 5,865,823 A | 2/1999 | Curro |
| 5,876,392 A | 3/1999 | Hisada |
| 5,876,531 A | 3/1999 | Jacobs et al. |
| 5,895,379 A | 4/1999 | Litchholt et al. |
| 5,897,545 A | 4/1999 | Kline et al. |
| 5,897,546 A | 4/1999 | Kido et al. |
| 5,902,296 A | 5/1999 | Fluyeras |
| 5,904,793 A | 5/1999 | Gorman et al. |
| 5,906,604 A | 5/1999 | Ronnberg et al. |
| 5,916,206 A | 6/1999 | Otsubo et al. |
| 5,919,178 A | 7/1999 | Widlund |
| 5,926,926 A | 7/1999 | Kato |
| 5,928,212 A | 7/1999 | Kline et al. |
| 5,940,887 A | 8/1999 | Rajala et al. |
| 5,941,865 A | 8/1999 | Otsubo et al. |
| 5,948,507 A | 9/1999 | Chen et al. |
| 5,957,906 A | 9/1999 | Roe et al. |
| 5,961,506 A | 10/1999 | Guidotti et al. |
| 5,961,761 A | 10/1999 | Heindel et al. |
| 5,971,970 A | 10/1999 | Carlbark et al. |
| 5,977,430 A | 11/1999 | Roe et al. |
| 5,984,911 A | 11/1999 | Siebers et al. |
| 6,007,527 A | 12/1999 | Kawaguchi et al. |
| 6,011,196 A | 1/2000 | Wang et al. |
| 6,017,621 A | 1/2000 | Hilston et al. |
| 6,020,535 A | 2/2000 | Blenke et al. |
| 6,030,373 A | 2/2000 | Van Gompel et al. |
| 6,036,805 A | 3/2000 | McNichols |
| 6,045,543 A | 4/2000 | Pozniak et al. |
| 6,049,915 A | 4/2000 | Malowaniec |
| 6,049,916 A | 4/2000 | Rajala et al. |
| 6,051,094 A | 4/2000 | Melbye et al. |
| 6,063,067 A | 5/2000 | Takizawa et al. |
| 6,066,774 A | 5/2000 | Roe |
| 6,068,620 A | 5/2000 | Chmielewski |
| 6,075,178 A | 6/2000 | La Wilhelm et al. |
| 6,077,379 A | 6/2000 | Herrin et al. |
| 6,080,909 A | 6/2000 | Osterdahl et al. |
| 6,083,212 A | 7/2000 | Kumasaka |
| 6,093,869 A | 7/2000 | Roe et al. |
| 6,098,203 A | 8/2000 | Rajala et al. |
| 6,107,538 A | 8/2000 | Young et al. |
| 6,107,539 A | 8/2000 | Palumbo et al. |
| 6,117,121 A | 9/2000 | Faulks et al. |
| 6,132,411 A | 10/2000 | Huber et al. |
| 6,140,551 A | 10/2000 | Niemeyer et al. |
| 6,142,986 A | 11/2000 | Lord et al. |
| 6,149,590 A | 11/2000 | Smith et al. |
| 6,149,636 A | 11/2000 | Roe et al. |
| 6,156,024 A | 12/2000 | Schulte et al. |
| 6,159,584 A | 12/2000 | Eaton et al. |
| 6,179,820 B1 | 1/2001 | Fernfors |
| 6,191,055 B1 | 2/2001 | Boyer, III et al. |
| 6,197,012 B1 | 3/2001 | Mishima et al. |
| 6,198,018 B1 | 3/2001 | Curro |
| 6,203,496 B1 | 3/2001 | Gael et al. |
| 6,213,991 B1 | 4/2001 | Kling et al. |
| 6,213,992 B1 | 4/2001 | Dreier |

(56) References Cited

U.S. PATENT DOCUMENTS

| | | |
|---|---|---|
| 6,218,593 B1 | 4/2001 | Torimae et al. |
| 6,222,091 B1 | 4/2001 | Beihoffer et al. |
| 6,224,961 B1 | 5/2001 | Hsueh et al. |
| 6,235,011 B1 | 5/2001 | O'Connell |
| 6,240,569 B1 | 6/2001 | Van Gompel et al. |
| 6,241,713 B1 | 6/2001 | Gross et al. |
| 6,255,236 B1 | 7/2001 | Cree et al. |
| 6,258,077 B1 | 7/2001 | Buell et al. |
| 6,260,211 B1 | 7/2001 | Rajala et al. |
| 6,264,643 B1 | 7/2001 | Toyoda |
| 6,266,557 B1 | 7/2001 | Roe et al. |
| 6,287,286 B1 | 9/2001 | Akin et al. |
| 6,287,287 B1 | 9/2001 | Eisberg |
| 6,307,119 B1 | 10/2001 | Cammarota et al. |
| 6,307,120 B1 | 10/2001 | Glaug |
| 6,312,420 B1 | 11/2001 | Sasaki et al. |
| 6,315,765 B1 | 11/2001 | Datta et al. |
| 6,328,725 B2 | 12/2001 | Femfors |
| 6,359,192 B1 | 3/2002 | Schmidt et al. |
| 6,364,863 B1 | 4/2002 | Yamamoto et al. |
| 6,367,089 B2 | 4/2002 | Van Gompel et al. |
| 6,368,312 B1 | 4/2002 | Otsubo et al. |
| 6,369,292 B1 | 4/2002 | Strack et al. |
| 6,371,951 B1 | 4/2002 | Koczab et al. |
| 6,372,951 B1 | 4/2002 | Ter-Ovanesyan et al. |
| 6,375,646 B1 | 4/2002 | Widlund et al. |
| 6,383,960 B1 | 5/2002 | Everett et al. |
| 6,392,116 B1 | 5/2002 | Beihoffer et al. |
| 6,394,991 B1 | 5/2002 | Takei et al. |
| 6,395,115 B1 | 5/2002 | Popp et al. |
| 6,395,955 B1 | 5/2002 | Roe et al. |
| 6,399,853 B1 | 6/2002 | Roe et al. |
| 6,402,730 B1 | 6/2002 | Malowaniec |
| 6,407,308 B1 | 6/2002 | Roe et al. |
| 6,409,858 B1 | 6/2002 | Popp et al. |
| 6,413,249 B1 | 7/2002 | Turi et al. |
| 6,414,216 B1 | 7/2002 | Malowaniec |
| 6,423,046 B1 | 7/2002 | Fujioka et al. |
| 6,428,525 B1 | 8/2002 | Malowaniec |
| 6,428,526 B1 | 8/2002 | Heindel et al. |
| 6,429,352 B1 | 8/2002 | Herrlein et al. |
| 6,432,098 B1 | 8/2002 | Kline et al. |
| 6,432,243 B1 | 8/2002 | Popp et al. |
| 6,432,248 B1 | 8/2002 | Popp et al. |
| 6,433,244 B1 | 8/2002 | Roe et al. |
| 6,437,213 B1 | 8/2002 | Schmidt et al. |
| 6,437,214 B1 | 8/2002 | Everett et al. |
| 6,440,117 B1 | 8/2002 | Itoh et al. |
| 6,447,497 B1 | 9/2002 | Olson |
| 6,447,628 B1 | 9/2002 | Couillard et al. |
| 6,448,202 B1 | 9/2002 | Miyazawa et al. |
| 6,454,751 B1 | 9/2002 | Olson |
| 6,455,753 B1 | 9/2002 | Glaug et al. |
| 6,458,115 B1 | 10/2002 | Lindqvist et al. |
| 6,461,343 B1 | 10/2002 | Schaefer et al. |
| 6,461,344 B1 | 10/2002 | Widlund et al. |
| 6,463,633 B1 | 10/2002 | Sangani et al. |
| 6,463,663 B1 | 10/2002 | Kanzawa |
| 6,464,635 B1 | 10/2002 | Jimenez Cerrato et al. |
| 6,465,379 B1 | 10/2002 | Cook et al. |
| D465,842 S | 11/2002 | Magee et al. |
| 6,476,289 B1 | 11/2002 | Buell et al. |
| 6,478,786 B1 | 11/2002 | Glaug et al. |
| 6,479,727 B1 | 11/2002 | Roe |
| 6,481,362 B2 | 11/2002 | Hietpas et al. |
| 6,494,873 B2 | 12/2002 | Karlsson et al. |
| 6,497,032 B2 | 12/2002 | Maxton et al. |
| 6,498,283 B1 | 12/2002 | Wada et al. |
| 6,498,953 B2 | 12/2002 | Roe et al. |
| 6,500,163 B2 | 12/2002 | Rönnberg et al. |
| 6,506,394 B1 | 1/2003 | Yahiaoui et al. |
| 6,506,959 B2 | 1/2003 | Hamajima et al. |
| 6,509,513 B2 | 1/2003 | Glaug et al. |
| 6,513,221 B2 | 2/2003 | Vogt et al. |
| 6,514,187 B2 | 2/2003 | Coenen et al. |
| 6,524,294 B1 | 2/2003 | Hilston et al. |
| 6,533,879 B2 | 3/2003 | Quereshi et al. |
| 6,540,731 B2 | 4/2003 | Magnussson et al. |
| 6,544,244 B1 | 4/2003 | Glaug et al. |
| 6,551,295 B1 | 4/2003 | Schmidt et al. |
| 6,566,578 B1 | 5/2003 | Glaug et al. |
| 6,569,139 B1 | 5/2003 | Datta et al. |
| 6,570,053 B2 | 5/2003 | Roe et al. |
| 6,570,058 B1 | 5/2003 | Fuchs et al. |
| 6,572,595 B1 | 6/2003 | Klemp et al. |
| 6,575,949 B1 | 6/2003 | Waksmundzki et al. |
| 6,575,952 B2 | 6/2003 | Kirk et al. |
| 6,579,275 B1 | 6/2003 | Pozniak et al. |
| 6,582,543 B1 | 6/2003 | Nilsson et al. |
| 6,590,136 B1 | 7/2003 | Young et al. |
| 6,595,976 B2 | 7/2003 | Jitoe et al. |
| 6,596,113 B2 | 7/2003 | Csida et al. |
| 6,602,238 B2 | 8/2003 | Takei et al. |
| 6,605,447 B2 | 8/2003 | Weiss et al. |
| 6,610,904 B1 | 8/2003 | Thomas et al. |
| 6,613,032 B2 | 9/2003 | Ronnberg et al. |
| 6,623,576 B2 | 9/2003 | Mitchell et al. |
| 6,626,881 B2 | 9/2003 | Shingu et al. |
| 6,626,882 B2 | 9/2003 | Hjorth |
| 6,627,394 B2 | 9/2003 | Kritzman et al. |
| 6,630,611 B1 | 10/2003 | Malowaniec |
| 6,632,209 B1 | 10/2003 | Chmielewski |
| 6,635,041 B1 | 10/2003 | Popp et al. |
| 6,635,135 B2 | 10/2003 | Kuen et al. |
| 6,642,431 B1 | 11/2003 | Gellerstedt et al. |
| 6,645,338 B1 | 11/2003 | Sangani et al. |
| 6,646,179 B1 | 11/2003 | Melius et al. |
| 6,646,180 B1 | 11/2003 | Chmielewski |
| 6,648,870 B2 | 11/2003 | Itoh et al. |
| 6,648,871 B2 | 11/2003 | Kusibojoska et al. |
| 6,649,810 B1 | 11/2003 | Minato et al. |
| 6,664,439 B1 | 12/2003 | Arndt et al. |
| 6,669,678 B2 | 12/2003 | Hermansson et al. |
| 6,676,645 B1 | 1/2004 | Bitterhof |
| 6,689,934 B2 | 2/2004 | Dodge, II et al. |
| 6,692,477 B2 | 2/2004 | Gibbs |
| 6,700,036 B2 | 3/2004 | Thomas et al. |
| 6,702,798 B2 | 3/2004 | Christoffel et al. |
| 6,709,423 B1 | 3/2004 | Herrlein et al. |
| 6,710,225 B1 | 3/2004 | Everett et al. |
| 6,713,660 B1 | 3/2004 | Roe et al. |
| 6,719,744 B2 | 4/2004 | Kinnear et al. |
| 6,723,035 B2 | 4/2004 | Franklin et al. |
| 6,726,669 B2 | 4/2004 | Shimada et al. |
| 6,726,670 B2 | 4/2004 | Almberg et al. |
| 6,727,403 B1 | 4/2004 | Ehrnsperger et al. |
| 6,733,483 B2 | 5/2004 | Raufman et al. |
| 6,736,804 B2 | 5/2004 | Robertson et al. |
| 6,740,071 B2 | 5/2004 | Gibbs |
| 6,749,860 B2 | 6/2004 | Tyrrell et al. |
| 6,755,808 B2 | 6/2004 | Balogh et al. |
| 6,761,711 B1 | 7/2004 | Fletcher et al. |
| 6,764,479 B2 | 7/2004 | Kusibojoska et al. |
| 6,770,065 B1 | 8/2004 | Sasaki et al. |
| 6,776,316 B2 | 8/2004 | Van Eperen et al. |
| 6,780,173 B2 | 8/2004 | Mishima et al. |
| 6,780,272 B2 | 8/2004 | Wood |
| 6,790,798 B1 | 9/2004 | Suzuki et al. |
| 6,803,496 B2 | 10/2004 | Elder et al. |
| 6,838,591 B2 | 1/2005 | Waksmundzki et al. |
| 6,840,928 B2 | 1/2005 | Datta et al. |
| 6,846,374 B2 | 1/2005 | Popp et al. |
| 6,849,067 B2 | 2/2005 | Fletcher et al. |
| 6,878,223 B2 | 4/2005 | Kuen et al. |
| 6,885,451 B2 | 4/2005 | Vogt et al. |
| 6,888,043 B2 | 5/2005 | Geiser et al. |
| 6,888,044 B2 | 5/2005 | Fell et al. |
| 6,888,143 B2 | 5/2005 | Vogt et al. |
| 6,891,080 B2 | 5/2005 | Minato et al. |
| 6,904,865 B2 | 6/2005 | Klofta et al. |
| 6,911,024 B2 | 6/2005 | Kusibojoska et al. |
| 6,921,647 B2 | 7/2005 | Kritzman et al. |
| 6,923,798 B2 | 8/2005 | Hedén et al. |
| 6,936,129 B2 | 8/2005 | Karami et al. |

(56) References Cited

U.S. PATENT DOCUMENTS

| | | |
|---|---|---|
| 6,945,968 B2 | 9/2005 | Svensson et al. |
| 6,946,585 B2 | 9/2005 | Brown |
| 6,953,452 B2 | 10/2005 | Popp et al. |
| 6,955,668 B2 | 10/2005 | Almberg et al. |
| 6,972,011 B2 | 12/2005 | Maeda et al. |
| 6,972,012 B1 | 12/2005 | Pozniak et al. |
| 6,981,951 B1 | 1/2006 | Rahe |
| 6,981,968 B2 | 1/2006 | Kusibojoska et al. |
| 6,991,622 B2 | 1/2006 | Nakaoka et al. |
| 6,994,761 B2 | 2/2006 | Klemp et al. |
| 7,000,260 B2 | 2/2006 | Rajala et al. |
| 7,001,368 B2 | 2/2006 | Otsubo |
| 7,002,054 B2 | 2/2006 | Allen et al. |
| 7,018,369 B2 | 3/2006 | Van Gompel et al. |
| 7,044,133 B2 | 5/2006 | Lohrengel et al. |
| 7,048,725 B2 | 5/2006 | Kling et al. |
| 7,060,058 B2 | 6/2006 | Otsubo et al. |
| D527,102 S | 8/2006 | Mills et al. |
| 7,087,046 B2 | 8/2006 | Van Gompel et al. |
| 7,090,667 B2 | 8/2006 | Fell et al. |
| D527,818 S | 9/2006 | Mills et al. |
| 7,156,939 B2 | 1/2007 | Vogt et al. |
| 7,163,745 B2 | 1/2007 | Mangold et al. |
| 7,166,094 B2 | 1/2007 | Glaug et al. |
| 7,172,585 B2 | 2/2007 | Sandin et al. |
| 7,175,910 B2 | 2/2007 | Ehrnsperger et al. |
| 7,195,622 B2 | 3/2007 | Lindström |
| 7,201,743 B2 | 4/2007 | Röhrl |
| 7,204,907 B2 | 4/2007 | Cree et al. |
| 7,217,261 B2 | 5/2007 | Otsubo et al. |
| 7,241,627 B2 | 7/2007 | Wilhelm et al. |
| 7,270,881 B2 | 9/2007 | Schmidt et al. |
| 7,285,178 B2 | 10/2007 | Mischler et al. |
| 7,314,465 B2 | 1/2008 | Van Gompel et al. |
| 7,314,752 B2 | 1/2008 | Kritzman et al. |
| 7,322,967 B2 | 1/2008 | Kondo |
| 7,331,946 B2 | 2/2008 | Shimada et al. |
| 7,332,642 B2 | 2/2008 | Liu |
| 7,344,525 B2 | 3/2008 | Linker, III et al. |
| 7,347,846 B2 | 3/2008 | Hermansson et al. |
| 7,368,027 B2 | 5/2008 | Schneider et al. |
| 7,373,698 B2 | 5/2008 | Erdman et al. |
| 7,378,567 B2 | 5/2008 | Mangold |
| 7,378,568 B2 | 5/2008 | Thomas et al. |
| 7,387,148 B2 | 6/2008 | Vogt et al. |
| 7,396,349 B2 | 7/2008 | Van Himbergen et al. |
| 7,396,585 B2 | 7/2008 | Schmidt et al. |
| 7,402,339 B2 | 7/2008 | Schmidt et al. |
| 7,411,110 B2 | 8/2008 | Sawyer et al. |
| 7,425,242 B2 | 9/2008 | Olsson et al. |
| 7,432,413 B2 | 10/2008 | Roe et al. |
| 7,435,245 B2 | 10/2008 | Wendelstorf et al. |
| 7,438,709 B2 | 10/2008 | Karami et al. |
| 7,449,014 B2 | 11/2008 | Oba et al. |
| 7,455,665 B2 | 11/2008 | Wendelstorf et al. |
| 7,462,754 B2 | 12/2008 | Malowaniec |
| 7,462,756 B2 | 12/2008 | Malowaniec |
| 7,482,505 B2 | 1/2009 | Stupperich et al. |
| 7,488,535 B2 | 2/2009 | Ehrnsperger et al. |
| 7,504,235 B2 | 3/2009 | Song |
| 7,524,313 B2 | 4/2009 | Kline et al. |
| 7,524,449 B2 | 4/2009 | Walsh et al. |
| 7,524,561 B2 | 4/2009 | Schmidt et al. |
| 7,527,618 B2 | 5/2009 | Benning et al. |
| 7,534,237 B2 | 5/2009 | Olson et al. |
| 7,534,481 B2 | 5/2009 | Seth et al. |
| 7,541,177 B2 | 6/2009 | Kritzman et al. |
| 7,544,628 B2 | 6/2009 | Stupperich et al. |
| 7,559,124 B2 | 7/2009 | Poulakis |
| 7,569,039 B2 | 8/2009 | Matsuda et al. |
| 7,569,041 B2 | 8/2009 | Stupperich et al. |
| 7,592,020 B2 | 9/2009 | Boga et al. |
| 7,604,624 B2 | 10/2009 | Veith et al. |
| 7,621,901 B2 | 11/2009 | Karami |
| 7,682,349 B2 | 3/2010 | Popp et al. |
| 7,687,680 B2 | 3/2010 | Fell et al. |
| 7,695,464 B2 | 4/2010 | Fletcher et al. |
| 7,699,825 B2 | 4/2010 | Nakagawa et al. |
| 7,713,371 B2 | 5/2010 | Lohrengel et al. |
| 7,718,021 B2 | 5/2010 | Venturino et al. |
| 7,722,590 B2 | 5/2010 | Tsuji et al. |
| 7,737,324 B2 | 6/2010 | LaVon et al. |
| 7,744,576 B2 | 6/2010 | Busam et al. |
| 7,744,713 B2 | 6/2010 | Blessing et al. |
| 7,749,211 B2 | 7/2010 | Van Gompel et al. |
| 7,750,203 B2 | 7/2010 | Becker et al. |
| 7,758,558 B2 | 7/2010 | Otsubo |
| 7,794,442 B2 | 9/2010 | Roehrl et al. |
| 7,794,839 B2 | 9/2010 | Schmidt et al. |
| 7,807,861 B2 | 10/2010 | Molander et al. |
| 7,819,851 B2 | 10/2010 | Karlsson |
| 7,837,662 B2 | 11/2010 | Nakagawa et al. |
| 7,838,721 B2 | 11/2010 | Chen |
| 7,838,722 B2 | 11/2010 | Blessing et al. |
| 7,846,383 B2 | 12/2010 | Song |
| 7,851,667 B2 | 12/2010 | Becker et al. |
| 7,851,669 B2 | 12/2010 | Nakagawa et al. |
| 7,857,801 B2 | 12/2010 | Hamall et al. |
| 7,863,498 B2 | 1/2011 | Roe et al. |
| 7,867,213 B2 | 1/2011 | Bandorf et al. |
| 7,906,065 B1 | 3/2011 | Brown et al. |
| 7,918,959 B2 | 4/2011 | Hornung et al. |
| 7,923,597 B2 | 4/2011 | Ponomarenko et al. |
| 7,935,299 B2 | 5/2011 | Walsh et al. |
| 7,943,537 B2 | 5/2011 | Vincent et al. |
| 7,947,467 B2 | 5/2011 | Kritzman et al. |
| 7,947,865 B2 | 5/2011 | Fossum et al. |
| 7,956,236 B2 | 6/2011 | Ponomarenko et al. |
| 7,982,088 B2 | 7/2011 | Roe et al. |
| 7,993,320 B2 | 8/2011 | Hornung et al. |
| 7,994,384 B2 | 8/2011 | Qin et al. |
| 8,016,806 B2 | 9/2011 | Hornung et al. |
| 8,017,827 B2 | 9/2011 | Hundorf et al. |
| 8,025,652 B2 | 9/2011 | Hornung et al. |
| 8,038,662 B2 | 10/2011 | Hornung et al. |
| 8,043,272 B2 | 10/2011 | Long et al. |
| 8,044,257 B2 | 10/2011 | Song |
| 8,083,724 B2 | 12/2011 | Bittner et al. |
| 8,088,967 B2 | 1/2012 | Underhill et al. |
| 8,100,173 B2 | 1/2012 | Hornung et al. |
| 8,138,388 B2 | 3/2012 | Elder et al. |
| 8,142,590 B2 | 3/2012 | Rejala et al. |
| 8,148,598 B2 | 4/2012 | Tsang et al. |
| 8,152,788 B2 | 4/2012 | Beckert et al. |
| 8,158,848 B2 | 4/2012 | Swerev et al. |
| 8,162,913 B2 | 4/2012 | Goates et al. |
| 8,180,603 B2 | 5/2012 | Blessing et al. |
| 8,187,240 B2 | 5/2012 | Busam et al. |
| 8,196,809 B2 | 6/2012 | Thorstensson |
| 8,202,390 B2 | 6/2012 | Malowaniec |
| 8,206,365 B2 | 6/2012 | Norrby |
| 8,206,533 B2 | 6/2012 | Hundorf et al. |
| 8,221,372 B2 | 7/2012 | Kouno et al. |
| 8,221,379 B2 | 7/2012 | Lam et al. |
| 8,221,672 B2 | 7/2012 | Brown et al. |
| 8,231,593 B2 | 7/2012 | Nakagawa et al. |
| 8,241,263 B2 | 8/2012 | Mills |
| 8,251,967 B2 | 8/2012 | Malowaniec |
| 8,258,366 B2 | 9/2012 | Wendelstorf |
| 8,263,820 B2 | 9/2012 | Carlucci et al. |
| 8,282,617 B2 * | 10/2012 | Kaneda ............ A61F 13/49011 604/385.01 |
| 8,292,865 B2 | 10/2012 | Hutson et al. |
| 8,298,205 B2 | 10/2012 | Norrby et al. |
| 8,303,562 B2 | 11/2012 | Hornung et al. |
| 8,319,005 B2 | 11/2012 | Becker et al. |
| 8,343,296 B2 | 1/2013 | Blessing et al. |
| 8,353,891 B2 | 1/2013 | Hornung et al. |
| 8,454,572 B2 | 6/2013 | Roe et al. |
| 8,454,782 B2 | 6/2013 | Ostertag |
| 8,466,336 B2 | 6/2013 | Carlucci et al. |
| 8,476,173 B2 | 7/2013 | Dovertie et al. |
| 8,496,637 B2 | 7/2013 | Hundorf et al. |
| 8,512,305 B2 | 8/2013 | Dziezok et al. |

(56) References Cited

U.S. PATENT DOCUMENTS

| | | |
|---|---|---|
| 8,518,539 B2 | 8/2013 | Meyer et al. |
| 8,552,252 B2 | 10/2013 | Hundorf et al. |
| 8,562,580 B2 | 10/2013 | Van Gompel et al. |
| 8,562,581 B2 | 10/2013 | Karami et al. |
| 8,585,666 B2 | 11/2013 | Weisman et al. |
| 8,616,867 B2 | 12/2013 | Brown et al. |
| 8,622,984 B2 | 1/2014 | Rajala et al. |
| 8,663,186 B2 | 3/2014 | Lam et al. |
| 8,668,975 B2 | 3/2014 | Westwood |
| 8,672,915 B2 * | 3/2014 | Kuwano ............ A61F 13/49011 604/385.3 |
| 8,708,990 B2 | 4/2014 | Beckert et al. |
| 8,747,379 B2 | 6/2014 | Fletcher et al. |
| 8,771,249 B2 | 7/2014 | Beckert et al. |
| 8,784,398 B2 | 7/2014 | Beckert et al. |
| 8,864,733 B2 | 10/2014 | Koenig et al. |
| 8,920,399 B2 | 12/2014 | Mills |
| 2001/0023341 A1 | 9/2001 | Karami |
| 2001/0025147 A1 | 9/2001 | Roe et al. |
| 2001/0034512 A1 | 10/2001 | Karlsson et al. |
| 2001/0042584 A1 | 11/2001 | Karami et al. |
| 2002/0019615 A1 | 2/2002 | Roe et al. |
| 2002/0045881 A1 | 4/2002 | Kusibojoska et al. |
| 2002/0062117 A1 | 5/2002 | Raufman et al. |
| 2002/0065503 A1 | 5/2002 | Guidotti |
| 2002/0111596 A1 | 8/2002 | Fletcher et al. |
| 2002/0115969 A1 | 8/2002 | Maeda et al. |
| 2002/0123733 A1 | 9/2002 | Itch et al. |
| 2002/0138056 A1 | 9/2002 | Kuen et al. |
| 2002/0138062 A1 | 9/2002 | Kuen et al. |
| 2002/0156441 A1 | 10/2002 | Sawyer et al. |
| 2002/0164658 A1 | 11/2002 | Weiss et al. |
| 2002/0177829 A1 | 11/2002 | Fell et al. |
| 2003/0004490 A1 | 1/2003 | Larsson et al. |
| 2003/0014025 A1 | 1/2003 | Allen et al. |
| 2003/0022581 A1 | 1/2003 | Tsai et al. |
| 2003/0023225 A1 | 1/2003 | Sayama |
| 2003/0055394 A1 | 3/2003 | Gibbs |
| 2003/0097113 A1 | 5/2003 | Molee |
| 2003/0100878 A1 | 5/2003 | Leak et al. |
| 2003/0105446 A1 | 6/2003 | Hutson et al. |
| 2003/0113507 A1 | 6/2003 | Niemeyer et al. |
| 2003/0114808 A1 | 6/2003 | Underhill et al. |
| 2003/0119404 A1 | 6/2003 | Belau et al. |
| 2003/0166293 A1 | 9/2003 | Kritzman et al. |
| 2003/0199843 A1 | 10/2003 | Kato et al. |
| 2004/0044324 A1 | 3/2004 | Swenson et al. |
| 2004/0102755 A1 | 5/2004 | Morman et al. |
| 2004/0122410 A1 | 6/2004 | Itch et al. |
| 2004/0133180 A1 | 7/2004 | Mori et al. |
| 2004/0153046 A1 | 8/2004 | Ito et al. |
| 2004/0158212 A1 | 8/2004 | Ponomarenko et al. |
| 2004/0172000 A1 | 9/2004 | Roe et al. |
| 2004/0243086 A1 | 12/2004 | Van Gompel et al. |
| 2004/0243089 A1 | 12/2004 | Veith et al. |
| 2005/0003143 A1 | 1/2005 | Ducauchuis et al. |
| 2005/0027279 A1 | 2/2005 | Minato et al. |
| 2005/0075618 A1 | 4/2005 | Kenmochi et al. |
| 2005/0113778 A1 | 5/2005 | Johansson et al. |
| 2005/0131287 A1 | 6/2005 | Kaylor et al. |
| 2005/0131378 A1 | 6/2005 | Sasaki et al. |
| 2005/0143709 A1 | 6/2005 | Lindstrom |
| 2005/0148960 A1 | 7/2005 | Price |
| 2005/0175269 A1 | 8/2005 | Ashton et al. |
| 2005/0228356 A1 | 10/2005 | LaVon et al. |
| 2005/0256494 A1 | 11/2005 | Datta |
| 2005/0256496 A1 | 11/2005 | Benning et al. |
| 2005/0273067 A1 | 12/2005 | Malowaniec et al. |
| 2006/0024433 A1 | 2/2006 | Blessing et al. |
| 2006/0025733 A1 | 2/2006 | Kikuchi et al. |
| 2006/0036230 A1 | 2/2006 | Mills et al. |
| 2006/0047259 A1 | 3/2006 | Erdman et al. |
| 2006/0058772 A1 | 3/2006 | Karami |
| 2006/0069379 A1 | 3/2006 | Van Gompel et al. |
| 2006/0121811 A1 | 6/2006 | Mangold et al. |
| 2006/0135923 A1 | 6/2006 | Boggs et al. |
| 2006/0135928 A1 | 6/2006 | Karlsson et al. |
| 2006/0135932 A1 | 6/2006 | Abuto et al. |
| 2006/0155254 A1 | 7/2006 | Sanz et al. |
| 2006/0167424 A1 | 7/2006 | Chang et al. |
| 2006/0184149 A1 | 8/2006 | Kasai et al. |
| 2006/0212010 A1 | 9/2006 | Roe et al. |
| 2006/0241560 A1 | 10/2006 | Chang et al. |
| 2006/0247596 A1 | 11/2006 | Van Dyke |
| 2006/0258250 A1 | 11/2006 | Mangold et al. |
| 2006/0276765 A1 | 12/2006 | Swerev et al. |
| 2006/0282053 A1 | 12/2006 | Rohrl |
| 2007/0000987 A1 | 1/2007 | Karlsson |
| 2007/0003993 A1 | 1/2007 | Kritzman et al. |
| 2007/0016155 A1 | 1/2007 | Chang et al. |
| 2007/0021728 A1 | 1/2007 | Speak |
| 2007/0038199 A1 | 2/2007 | Erdman et al. |
| 2007/0044903 A1 | 3/2007 | Wisneski et al. |
| 2007/0048815 A1 | 3/2007 | Song |
| 2007/0049892 A1 | 3/2007 | Lord et al. |
| 2007/0049896 A1 | 3/2007 | Mills |
| 2007/0066950 A1 | 3/2007 | Nelson |
| 2007/0073260 A1 | 3/2007 | Roe |
| 2007/0073262 A1 | 3/2007 | Babusik et al. |
| 2007/0128589 A1 | 6/2007 | Sanders et al. |
| 2007/0208317 A1 | 9/2007 | Krautkramer et al. |
| 2007/0239131 A1 | 10/2007 | Hermansson et al. |
| 2007/0255246 A1 | 11/2007 | Schneider |
| 2007/0293833 A1 | 12/2007 | Wennerback |
| 2007/0293835 A1 | 12/2007 | Roehrl et al. |
| 2008/0026178 A1 | 1/2008 | Stupperich et al. |
| 2008/0051747 A1 | 2/2008 | Cohen |
| 2008/0086060 A1 | 4/2008 | Kritzman et al. |
| 2008/0103414 A1 | 5/2008 | Song |
| 2008/0108964 A1 | 5/2008 | Edwall |
| 2008/0125735 A1 | 5/2008 | Busam et al. |
| 2008/0134487 A1 | 6/2008 | Hartono |
| 2008/0147031 A1 | 6/2008 | Long et al. |
| 2008/0161767 A1 | 7/2008 | Sandin et al. |
| 2008/0208152 A1 | 8/2008 | Eckstein et al. |
| 2008/0249493 A1 | 10/2008 | Kobayashi et al. |
| 2008/0274014 A1 | 11/2008 | Jumonville et al. |
| 2008/0281286 A1 | 11/2008 | Petersen |
| 2008/0287897 A1 | 11/2008 | Guzman Reyes et al. |
| 2008/0287898 A1 | 11/2008 | Guzman Reyes et al. |
| 2008/0287899 A1 | 11/2008 | Morrell-Schwartz et al. |
| 2008/0312618 A1 | 12/2008 | Hundorf et al. |
| 2008/0312628 A1 | 12/2008 | Hundorf et al. |
| 2008/0312631 A1 | 12/2008 | Okuda |
| 2009/0143757 A1 | 6/2009 | Hornung et al. |
| 2009/0177176 A1 | 7/2009 | Saito |
| 2009/0198205 A1 | 8/2009 | Malowaniec et al. |
| 2009/0275071 A1 | 11/2009 | Brusilovsky et al. |
| 2009/0275911 A1 | 11/2009 | Hornung et al. |
| 2009/0299322 A1 | 12/2009 | Faulks et al. |
| 2009/0312736 A1 | 12/2009 | Schroer, Jr. et al. |
| 2009/0326503 A1 | 12/2009 | Lakso et al. |
| 2010/0051170 A1 | 3/2010 | Nakakado |
| 2010/0063468 A1 | 3/2010 | Lehto et al. |
| 2010/0065199 A1 | 3/2010 | Hornung et al. |
| 2010/0076390 A1 | 3/2010 | Norrby et al. |
| 2010/0108251 A1 | 5/2010 | Malowaniec |
| 2010/0136707 A1 | 6/2010 | Kritzman et al. |
| 2010/0163161 A1 | 7/2010 | Gilgenbach et al. |
| 2010/0168705 A1 | 7/2010 | Stabelfeldt et al. |
| 2010/0198178 A1 | 8/2010 | Litvay |
| 2010/0234820 A1 | 9/2010 | Tsai |
| 2010/0290948 A1 | 11/2010 | Song |
| 2010/0292663 A1 | 11/2010 | Lavon et al. |
| 2010/0318055 A1 | 12/2010 | Hornung et al. |
| 2011/0071488 A1 * | 3/2011 | Kuwano ............ A61F 13/49001 604/385.3 |
| 2001/0098668 | 4/2011 | Thorson et al. |
| 2011/0098668 A1 | 4/2011 | Thorson et al. |
| 2011/0123775 A1 | 5/2011 | Westwood |
| 2011/0130275 A1 | 6/2011 | Weismantel et al. |
| 2011/0144610 A1 | 6/2011 | Karlson et al. |
| 2011/0146892 A1 | 6/2011 | Ostertag |
| 2011/0160692 A1 | 6/2011 | Wilkes et al. |

(56) References Cited

U.S. PATENT DOCUMENTS

| | | |
|---|---|---|
| 2011/0208140 A1 | 8/2011 | Roe et al. |
| 2011/0208142 A1 | 8/2011 | Roe et al. |
| 2012/0028777 A1 | 2/2012 | Knecht |
| 2012/0053552 A1 | 3/2012 | Van Gompel et al. |
| 2012/0065607 A1 | 3/2012 | Konig et al. |
| 2012/0165777 A1 | 6/2012 | Beckert et al. |
| 2012/0172828 A1 | 7/2012 | Koenig et al. |
| 2012/0310193 A1 | 12/2012 | Ostertag |
| 2013/0144245 A1 | 6/2013 | Roe |
| 2013/0211365 A1 | 8/2013 | Rajala et al. |
| 2013/0277154 A1 | 10/2013 | Fritz et al. |
| 2013/0281957 A1 | 10/2013 | Fritz et al. |
| 2013/0296739 A1 | 11/2013 | Schultz |
| 2013/0345657 A1 | 12/2013 | Nelson et al. |
| 2014/0046286 A1 | 2/2014 | Homann et al. |
| 2014/0121487 A1 | 5/2014 | Faybishenko et al. |
| 2015/0011958 A1* | 1/2015 | Yoshioka .............. A61F 13/496 604/385.16 |
| 2015/0297421 A1 | 10/2015 | Nelson |

FOREIGN PATENT DOCUMENTS

| | | |
|---|---|---|
| WO | 2009117492 A2 | 9/2009 |
| WO | 2015168032 A1 | 11/2015 |

OTHER PUBLICATIONS

Notification of Transmittal of the International Search Report and the Written Opinion of the International Searching Authority, or the Declaration; International Application No. PCT/US2015/026104; Medline Industries, Inc. (Nelson), Aug. 3, 2015.

Notification of Transmittal of the International Search Report and the Written Opinion of the International Searching Authority, or the Declaration; International Application No. PCT/US/2015/035461; Medline Industries, Inc. (Nelson), Sep. 21, 2015.

Notification of Transmittal of the International Search Report and the Written Opinion of the International Searching Authority, or the Declaration; International Application No. PCT/US/2015/035467; Medline Industries, Inc. (Nelson), Sep. 21, 2015.

Chef Steps "How Knives Cut" (https://www.chefsteps.com/activities/how-knives-cut).

* cited by examiner

STRETCH BREATHABLE PROTECTIVE ABSORBENT ARTICLE USING BILAMINATE

This application is a continuation-in-part of commonly owned U.S. patent application Ser. No. 14/257,481 (filed Apr. 21, 2014), which is incorporated herein by reference.

FIELD OF THE INVENTION

The present invention relates a disposable absorbent article in an underwear or pull-up style. More particularly, the invention relates to protective underwear that makes use of breathable laminate material having two layers.

BACKGROUND OF THE INVENTION

Millions of people of all ages suffer from incontinence of the bowel or bladder. Whether an infant, adult, or elderly person, the underlying cause of incontinence varies but the method of treatment typically involves use of absorbent article products. Adult incontinent briefs, disposable diapers and underpads can alleviate some of the emotional and physical discomfort of incontinence by absorbing and containing liquid and other discharges from the human body to prevent body and clothing soiling.

A disadvantage of known disposable undergarments is that they are often constructed from materials that are designed to capture urine and other exudates and prevent leakage, but are not breathable. Consequently, moisture may become trapped between the wearer and the disposable undergarment leading to discomfort and irritation. Further, as disposable undergarments are intended to replace traditional undergarments, disposable undergarments must be constructed to permit the wearer to be repeatedly put-on and pull-off the garment as necessary until such time as the garment is ready for disposal.

Disposable protective underwear products are known in the art. Such disposable underwear products rely on retractive forces that are provided by elastics, such as spandex strands. It is also known to use stretch elastic laminates that replace the spandex strands so as to provide better a fit to the wearer and improved discretion. Some products are created from a co-extruded elastic layer made during the nonwoven manufacturing process to provide a product with improved breathability.

Widlund, et al., U.S. Pat. No. 6,375,646 teaches a disposable diaper including an elongated absorbent pad, inner and outer casing layers and an elastically stretchable region in at least one of the front and back portions of the disposable diaper. The crotch portion of the disposable diaper is not stretchable. The combined stretchable and non-stretchable regions are designed to hold the absorbent material against the wearer's body to prevent leakage.

Norrby, et al., U.S. Pat. No. 8,298,205 teaches an elastically stretchable laminate that includes a first non-elastic nonwoven web, a second non-elastic nonwoven web and an elastic film between the first and the second nonwoven webs. The laminate is rendered elastic in a first direction by incremental stretching and partial tearing of the first and second nonwoven webs.

Thorson, et al., U.S. Patent Application Publication No. 2011/0098668, teaches a disposable absorbent garment employing elastomeric film laminate body panels. The laminate can include an elastomeric film and nonwoven layers, and inner and outer surfaces adhered to nonwoven and elastomeric film layers.

Stablefeldt, et al., U.S. Patent Application Publication No. 2010/0168705, teaches disposable absorbent garments employing elastomeric film laminates with deactivated regions. A portion of the disposable garment includes laminated elastomeric and non-elastomeric polymeric film layers and a nonwoven layer. An absorbent member extends partially through the laminated layers.

Gilgenback U.S. Patent Application Publication No. 2010/0163161 teaches a process for making disposable absorbent garments employing elastomeric film laminates with deactivated regions. A portion of the disposable garment includes laminated elastomeric and non-elastomeric polymeric film layers and a nonwoven layer. An absorbent member extends partially through the laminated layers.

Kielpikowski, et al., U.S. Pat. No. 4,842,596, teaches a method for making a breathable elastic fabric composite and personal article incorporating same. A liquid impermeable elastomeric film is sandwiched between pairs of nonwoven sheets. The elastomeric film is a partially stretched condition and bonded to the nonwoven sheets. The resulting laminated sheets create gathers that form breathable apertures.

Klemp, et al., U.S. Pat. No. 6,994,761 teaches a disposable diaper and process for making the same. The diaper includes inner and outer portions that are ultrasonically bonded to create the vent sites or apertures through a layer of stretchable, breathable material.

BRIEF DESCRIPTION OF THE FIGURES

Advantages of the invention will become apparent upon reading the following detailed description and upon reference to the drawings.

DETAILED DESCRIPTION

Figure 1:
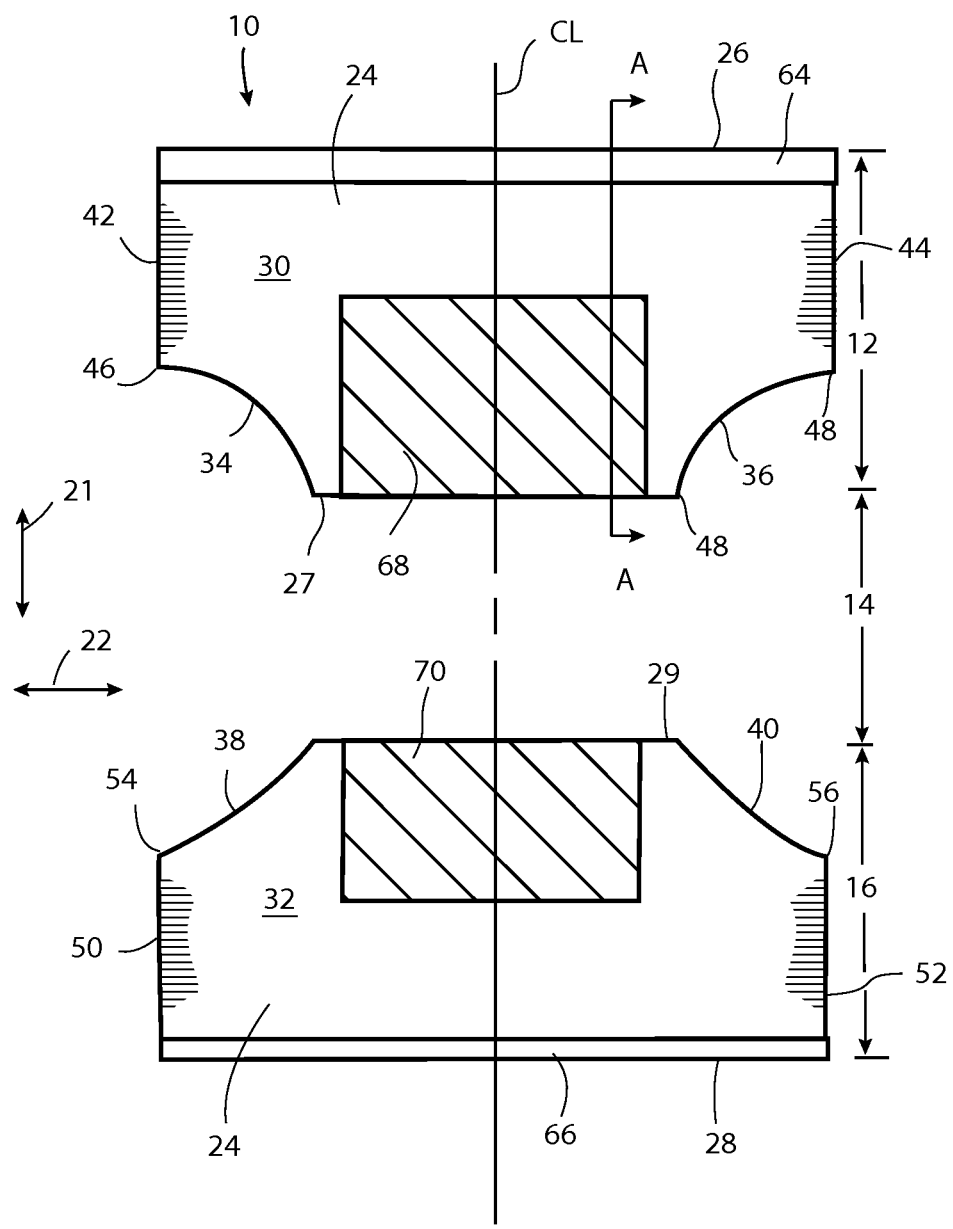
FIG. 1 is a top plan view of laminate portions of an absorbent article in a substantially flat un-contracted position according to an embodiment of the invention.

Absorbent articles as described herein generally include a moisture-pervious inner layer, an absorbent layer, and a moisture-impervious outer layer. Although the remainder of the description will be specifically directed to adult incontinence articles, such as disposable diapers or briefs, it is to be understood that the embodiments may also be implemented using other absorbent articles and that the properties and uses described below apply to these other absorbent articles as well. Throughout this application, the terms absorbent article, diaper or brief are used interchangeably. However, it should be understood that the terms diaper or brief are intended to include other absorbent articles, such as training pants, incontinence pads, etc., as would be understood by one of ordinary skill in the art.

As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, proximal and distal, and the like may be used solely to distinguish one entity or action from another entity or action without necessarily requiring or implying any actual such relationship or order between such entities or actions.

As used herein, the following terms have the following meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Breathable" when used in describing a layer or multi-layer laminate means that the layer has the ability to allow moisture vapor to be transmitted through the material. Breathable layers may be air permeable, but it is not necessary to be air permeable to be breathable. In addition, breathable layers may be liquid permeable or liquid impermeable.

"Disposable" refers to articles that are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Fiber" refers to a continuous or discontinuous member having a high ratio of length to diameter or width. Thus, a fiber may be a filament, a thread, a strand, a yarn, or any other member or combination of these members.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as meltblowing processes, spunbonding processes, air laying processes, and bonded carded web processes.

These terms may be defined with additional language elsewhere in the specification.

FIGS. 1, 5-7 and 9 illustrate a plan view of the absorbent article 10 in a substantially flat un-contracted state. As shown in these figures, the absorbent article 10 generally consists of several layers, including an inner layer, an absorbent layer, and an outer layer. The inner layer faces a wearer and contacts the skin of the wearer when the absorbent article 10 is secured to the wearer. The inner layer may comprise a topsheet that is composed of a moisture-pervious fabric suitable to allow bodily discharge to pass through the inner layer and be absorbed by the absorbent layer. Non-limiting examples of materials suitable to form the topsheet include polypropylene, polyethylene, polyester, materials having hydrophobic properties, combinations thereof and/or the like. Additionally, the topsheet can be treated with a hydrophilic finish to improve pass through of liquids to diaper layers beneath the inner layer. Non-limiting examples of suitable hydrophilic finishes include stearic acid, melamine-based chemicals, fluorocarbon chemicals, and silicon based chemicals.

The plan view of FIGS. 1, 5-7 and 9 is shown from the top or patient contacting side of the absorbent article. As illustrated in these figures, a particular embodiment of a disposable absorbent article 10 of the present invention defines a longitudinal direction 21 parallel to a centerline CL and a transverse direction 22 perpendicular to the longitudinal direction. The absorbent article comprises a front section 12, a rear section 16, and a crotch section 14.

Referring to FIG. 1, the absorbent article includes a film layer 24 comprising a laminate film. The laminate film may be divided into two sections such that the film layer 24 forms at least part of the front section 12 and rear section 16. The front film section 30 is spaced apart from the rear film section 32 such that they are separated in the crotch section 14.

The front film section 30 defines a front end edge 26 and a front crotch edge 27 parallel to and longitudinally spaced from the front end edge 26. The rear film section 32 defines a rear end edge 28 longitudinally opposite the front end edge 26 and a rear crotch edge 29 parallel to and longitudinally spaced from the rear end edge 28. The front film section defines opposed front leg edges 34 and 36, and the rear film section defines opposed rear leg edges 36 and 38.

The front film section 30 further defines first and second transversely opposed front side edges 42 and 44. The first front side edge 42 extends in the longitudinal direction 21 from the front end edge 26 to a front intersection point 46 where the first front side edge intersects the first front leg edge 34. The second front side edge 44 extends in the longitudinal direction 21 from the front end edge 26 to a front intersection point 48 where the first front side edge intersects the second front leg edge 36. The rear film section 32 also defines first and second transversely opposed back side edges 50 and 52. The first back side edge 50 extends in the longitudinal direction 21 from the back end edge 28 to a rear intersection point 54 where the first rear side edge 50 intersects the first rear leg edge 38, and the second back side edge 52 extends in the longitudinal direction 21 from the back end edge 28 to a rear intersection point 56 where the second rear side edge 52 intersects the second rear leg edge 40.

In particular embodiments, the front section 30 is constructed at least in part of a laminate 24 that comprises a polymeric film layer 62 and at least one nonwoven layer 60 (FIG. 2), wherein both the polymeric film layer 62 and the nonwoven layer 60 extend substantially throughout the area of the laminate 24.

In its completed form as used by a wearer, the absorbent article includes a first side seam at which the first front side edge 42 is attached to the first back side edge 50 and which defines a first side seam length. The article further includes a second side seam at which the second front side edge 44 is attached to the second back side edge 52 and which defines a second side seam length. The article is accordingly formed into a brief or pull-up style disposable absorbent article.

Figure 2:
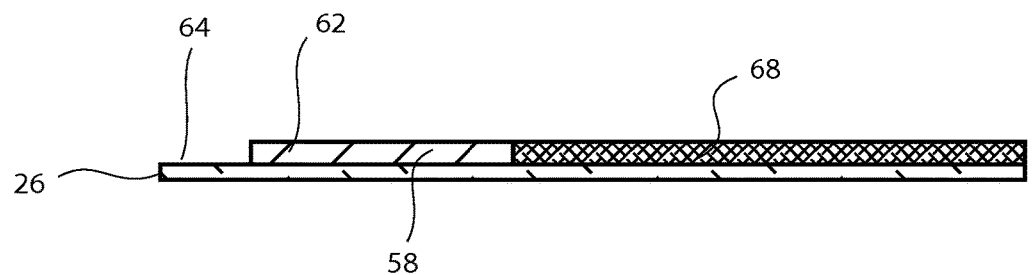
FIG. 2 is a cross-sectional view of the laminate of FIG. 1 along sectional line A-A.

FIG. 2 shows a cross-sectional view of the laminate 24 along line A-A. In one embodiment, the laminate 24 comprises a first nonwoven layer 58 superposed on the bottom surface of the polymeric film 62 such that the polymeric film 62 and the first nonwoven layer 58 extend substantially through the area of the laminate 24. The polymeric film layer may be a block copolymer. A portion 64 of the bottom or outer layer of nonwoven 58 may extend beyond the polymeric film 62 along front end edge 26. A further portion 66 of the bottom or outer layer of nonwoven 58 may extend beyond the polymeric film 62 along rear end edge 28.

Figure 3:
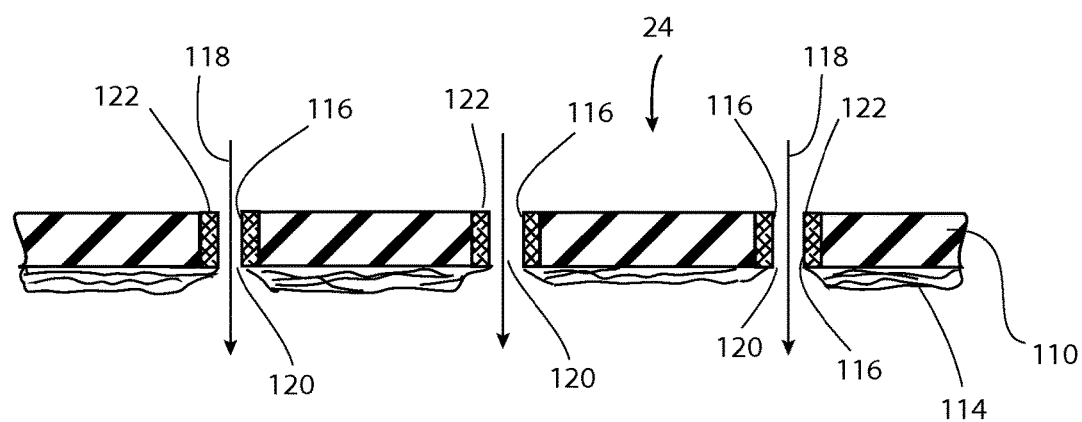
FIG. 3 is a cross-sectional view of a breathable laminate according to an embodiment of the invention.
Figure 4:
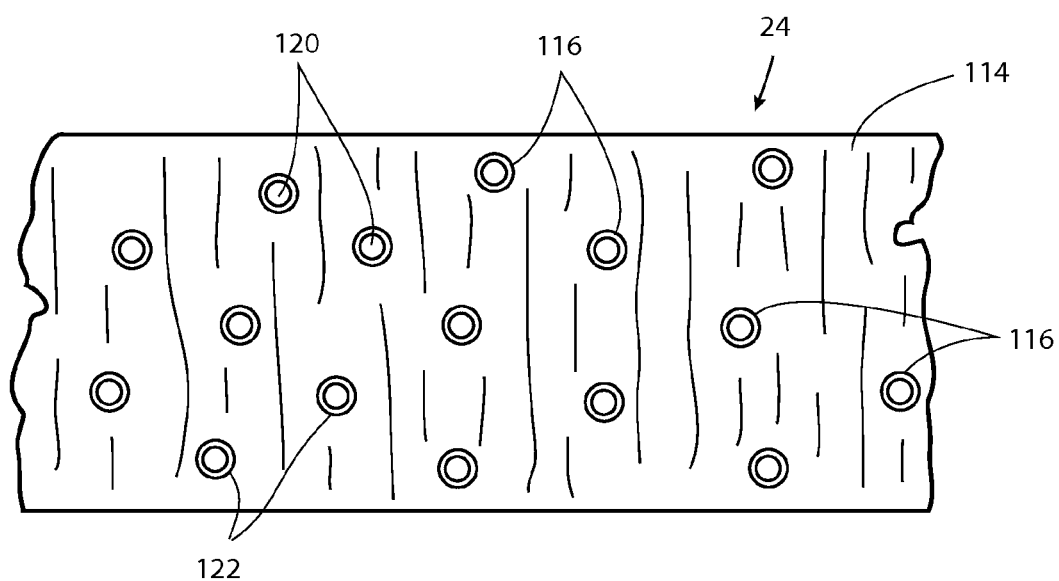
FIG. 4 is a top view of the laminate of FIG. 3.

As shown in FIGS. 3-4, the laminate 24 may be formed of a breathable cloth-like elastic nonwoven laminar fabric by attaching a liquid impermeable and non-self-adhering elastomeric film or nonwoven carrier sheet 110 to a nonwoven facing sheet 114 and bonding the facing sheet 114 and elastomeric film 110 together by autogenous bonds, such as ultrasonically or thermally-generated bonds at spaced apart sites 116, thereby forming breathable apertures 120 through the carrier sheet which laminate the carrier and facing sheet together at the spaced apart sites 116.

In an embodiment of the present invention, the facing sheet 114 and the elastomeric film 110 are ultrasonically bonded at sites 116. The ultrasonic bonding process creates a bond region 122 where the material from the facing sheet 114 and elastomeric film 110 mix together to form a bond. The ultrasonic bonding process may be configured such that it generates a through passage 120 generally within the confines of the bond region 122 in order to provide for the passage of water vapor 118 and give breathability to the laminate 24.

Figure 13:
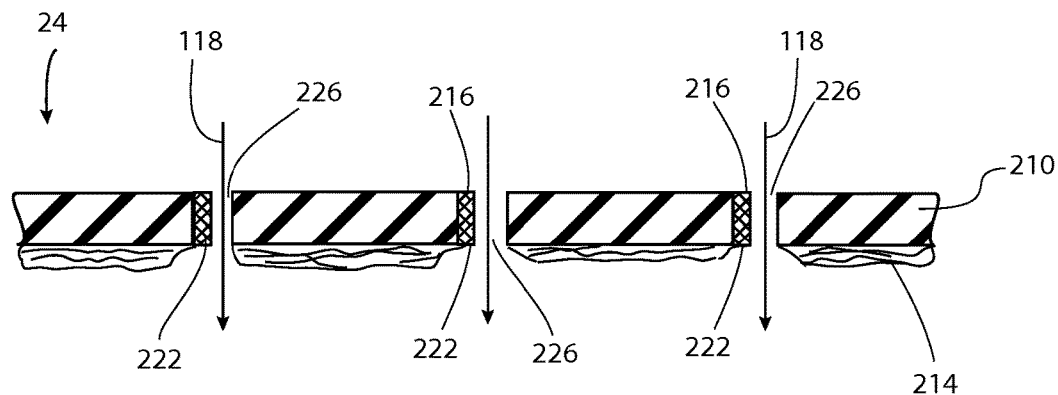
FIG. 13 is a cross-sectional view of a breathable laminate for use in a further embodiment of the invention.
Figure 14:
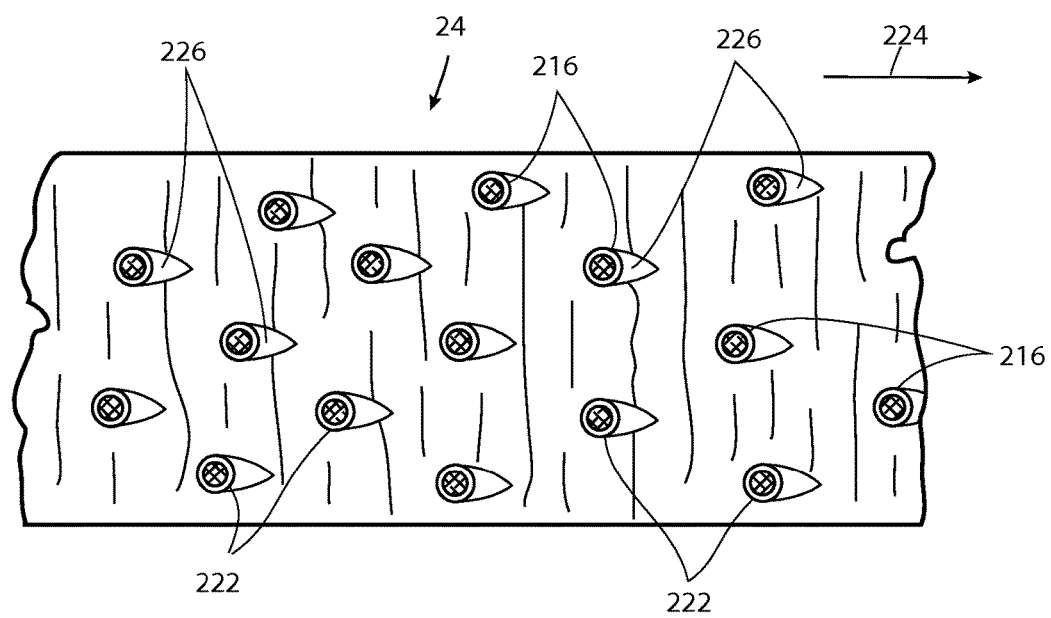
FIG. 14 is a top view of the laminate of FIG. 13.

In an alternative embodiment as illustrated in FIGS. 13-14, the facing sheet 214 and the elastomeric film 210 are ultrasonically bonded at sites 216. The ultrasonic bonding process creates a bond region 222 where the material from the facing sheet 214 and elastomeric film 210 mix together to form a bond. The ultrasonic bonding process may be conducted while the sheet is moving in a direction 224 such that a trailing tear 226 forms in the laminate generally outside and adjacent to the bond region 222. These trailing tears 226 provide through openings for the passage of water vapor 118 and give breathability to the laminate 24. While the bond regions 222 and trailing tears 226 are shown in FIGS. 13-14 as being of a size and shape sufficiently large to illustrate the structure of the bonded laminate, one of skill in the art will understand that these may be of any appropriate size and shape and may be sufficiently small that they are not be readily apparent without the use of magnification.

Alternatively, the laminate 24 can also be constructed such that the web is not made breathable during the ultrasonic laminating process, but rather has breathability imparted through a needling, slitting or die treatment process after formation of the complete laminate.

Referring again to FIG. 1, at least a portion 68 of the front film section 30 is non-elastomeric, and at least a portion 70 of the rear film section 32 is non-elastomeric. In FIGS. 1, 5-7 and 9 non-elastomeric or partially elastomeric regions are indicated by a pattern of hash lines, which lines are continuous if the non-elastomeric regions are exposed, and which lines are dashed if the non-elastomeric regions are concealed by an overlying component. In one preferred approach, as shall be described in more detail below, the entire laminate 24 is constructed of an elastomeric film laminate which includes an elastomeric film layer and at least one nonwoven facing layer, and a portion of the laminate has been "deactivated" or "deadened" to render it non-elastomeric.

As used herein, "elastomeric" refers to a material or composite which can be elongated by at least 50 percent of its relaxed length and which will recover, upon release of the applied force, at least 50 percent of its elongation. It is generally preferred that the elastomeric material or composite be capable of being elongated by at least 100 percent, more preferably by at least 200 percent, of its relaxed length and recover, upon release of an applied force, at least 50 percent of its elongation. "Non-elastomeric" refers to a material or composite that is non-extensible, or that is extensible but will recover no more than 20 percent of its elongated length after release of an applied elongating force. "Non-extensible" refers to a material that cannot stretch or extend by more than 25 percent of its relaxed length without fracture upon application of a biasing force. "Partially elastomeric" refers to a material or composite which can be elongated by at least 50 percent of its relaxed length and which will recover, upon release of the applied force, more than 20 percent but less than 50 percent of its elongation.

"Deactivated" as used herein to describe a material, region of a material, or regions of a material means that the material, region, or regions of material has been treated in some way to substantially destroy the elastic properties of the material, region, or regions, rendering the material, region, or regions non-elastomeric.

Deactivation of the non-elastic portions 68, 70 may be accomplished by a deactivation unit to create deactivated regions in the elastomeric film laminate 24. The deactivation can be accomplished by any of a variety of means. Frequently, some form of energy is applied to deactivate the non-elastic regions 68, 70, such as pressure, heat, ultrasonic energy, combinations thereof, and the like. Techniques employing pressure, heat, and ultrasonic energy are known in the art. The deactivation can occur in a variety of patterns. For example, the deactivating energy could be applied in a solid pattern, a series of vertical stripes, horizontal stripes, or diagonal stripes, a series of squares or dots, or other suitable pattern.

Figure 5:
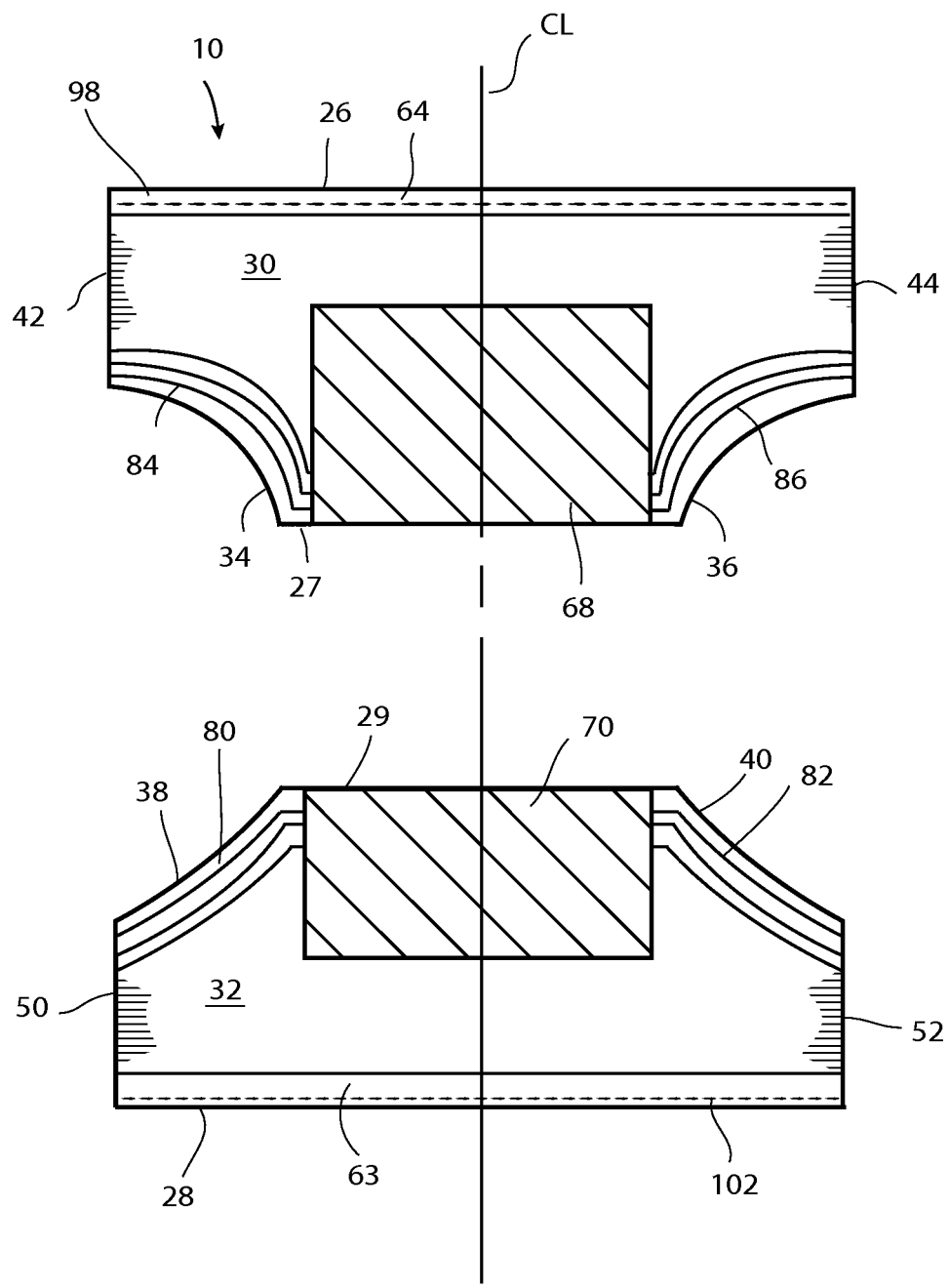
FIG. 5 is a top plan view of an embodiment of the absorbent article of FIG. 1 in a substantially flat un-contracted position and further including leg and waist elastics.

In embodiments of the present invention as illustrated in FIG. 5, the absorbent article 10 comprises a first rear leg elastic member 80 attached to an inside surface of the rear film section 32 adjacent at least a portion of the first rear leg edge 38, and a second back leg elastic member 82 to an inside surface of the rear film section 32 adjacent at least a portion of the second rear leg edge 40. In further embodiments, the absorbent article 10 comprises a first front leg elastic member 84 attached to an inside surface of the rear film section 30 adjacent at least a portion of the first front leg edge 34, and a second front leg elastic member 86 attached to attached to an inside surface of the rear film section 30 adjacent at least a portion of the second front leg edge 36. Each leg elastic member 80, 82, 84, 86 can comprise a single strand, ribbon, or strip of elastomeric material, or each can comprise two or more strands, ribbons, or strips, such as, for example, three strands (as depicted in FIG. 5). The leg elastic members 80, 82, 84, 86 may be glued in place or otherwise adhered to a top surface of nonwoven layer 60.

As illustrated in FIG. 5, rear leg elastic member 80, 82 may extend from side edges 50, 52 of the rear film section 32 along rear leg edges 38, 40 to side edges of the non-elastic portion 70 of the rear film section. Alternatively, the rear leg elastic member 80, 82 may extend across part or the entire non-elastic portion 70. Likewise, front leg elastic member 84, 86 may extend from side edges 42, 44 of the front film section 30 along front leg edges 34, 36 to side edges of the non-elastic portion 68 of the front film section. Alternatively, the front leg elastic member 84, 86 may extend across part or the entire non-elastic portion 68.

For example, the first rear leg elastic member 80 and the second rear leg elastic member 82 may form part of a single, integral back elastic member that extends from the first rear side edge 50 transversely over the non-elastic portion 70 to the second rear side edge 52. Similarly, in certain embodiments, the first front leg elastic member 84 and the second front leg elastic member 86 form part of a single, integral front elastic member that extends from the first front side edge 42 transversely over the non-elastic portion 68 to the second front side edge 44.

In embodiments, as illustrated in FIG. 5, the extension 64 of the outer nonwoven layer 58 (see FIGS. 1-2) of the front portion 30 may be folded over the top of inner nonwoven layer 60 to define the front end edge 26. A similar extension 63 of the outer layer of nonwoven of the rear laminate 32 may be folded over the top of inner nonwoven layer to define the rear end edge 28.

The absorbent article 10 may further include a front waist elastic member 98 positioned within the front fold 64 and a back waist elastic member 102 positioned within the back fold 63. In alternative embodiments, no front waist fold or back waist fold is included; in such embodiments, opposite end edges of the laminate sections 30, 32 would define the front end edge 26 and back end edge 28, respectively. Each waist elastic member 98, 102 may comprise a single strand, ribbon, or strip of elastomeric material, or each can comprise two or more strands, ribbons, or strips.

Figure 6:
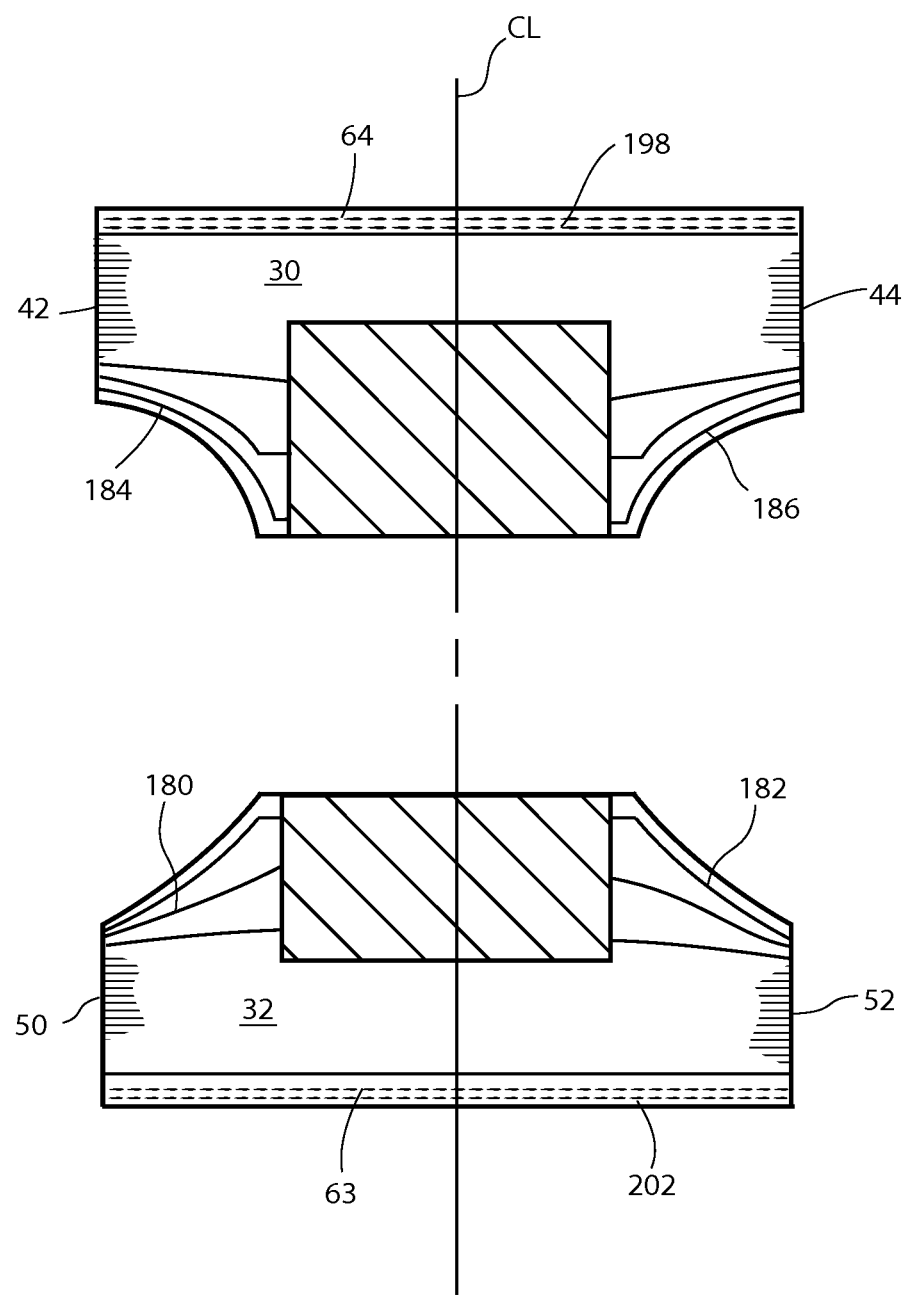
FIG. 6 is an alternative embodiment of the absorbent article of FIG. 5.

FIG. 6 illustrates further embodiments in which the leg elastic members 180, 182, 184, 186 comprises a series of elastic strands. The illustrated embodiment shows three such strands, but more or fewer strands may be used. The leg elastics may be applied in a curved fashion. At the side edges 42, 44, 50, 52 of the diaper, the leg elastics are generally parallel, and each of the independent leg elastics are then curved towards the respective non-elastic portions 68, 70 of the film sections 30, 32, and increasingly separated in distance from one another the closer the leg elastics get to the non-elastic film portions. Also as shown in FIG. 6, the waist elastic members 198, 202 may comprise multiple elastic strands.

Figure 7:
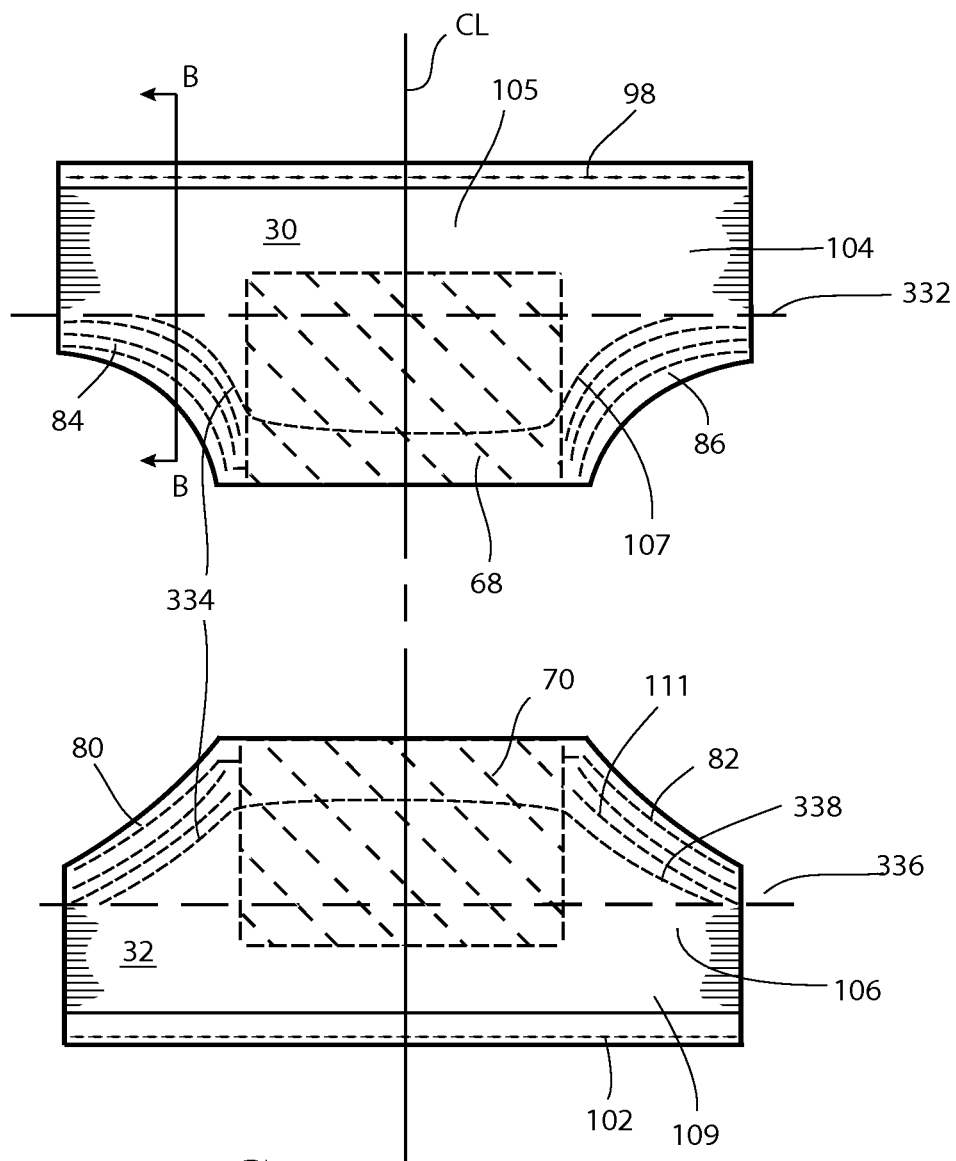
FIG. 7 is a top plan view of an embodiment of the absorbent article of FIG. 1 in a substantially flat un-contracted position and further including a covering nonwoven layer.
Figure 8:
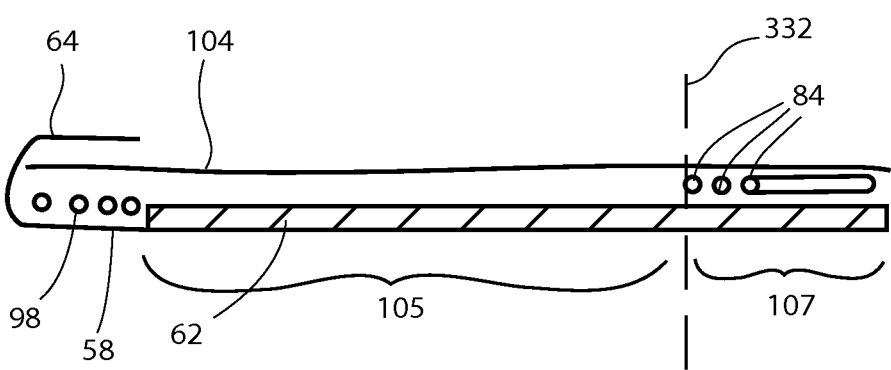
FIG. 8 is a cross-sectional view of the absorbent article of FIG. 7 along sectional line B-B.

As illustrated in FIGS. 7-8, an additional covering nonwoven layer 104 may be attached to a top surface of the polymeric film layer 62 that comprises the top layer of the front laminate section 30. Additionally, a further covering nonwoven layer 106 may be attached to a top surface of the polymeric film layer 62 that comprises the top layer of the rear laminate section 32. The covering nonwoven layers 104, 106 are placed on top of laminate sections so that they at least in part cover the leg elastic elements. The covering nonwoven layers may be bonded to the film laminate 24 in the region 105 where the leg elastics 80, 82, 84, 86 are not present and may be glued to the elastics and/or the polymeric film layer 62 in region 107 where the elastics are located.

The front 30 and rear 32 laminate sections may each be separated into two or more areas that are characterized by the manner in which the covering nonwoven layers 104, 106 are attached to the polymeric film layer 62. The front section 30 may have a first bonded portion 105 in which the covering nonwoven 104 is attached to the film laminate 24 by autogenous bonds, such as ultrasonically or thermally-generated bonds at spaced apart sites. The rear section 32 may have a corresponding bonded portion 109.

Figure 9:
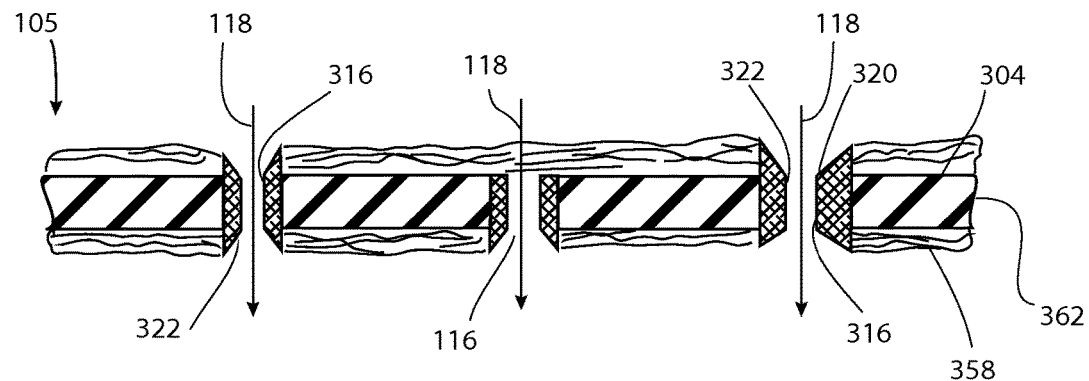
FIG. 9 is a cross-sectional view of an embodiment of a laminate used in a portion of the absorbent article illustrated in FIG. 7.

As illustrated in FIG. 9, the spaced apart bonding sites 316 of areas 105 form breathable apertures 320 through the outer nonwoven layer 358, polymeric film layer 362 and covering nonwoven layer 304. The ultrasonic bonding process creates a bond region 322 where the material from the outer facing sheet 358, polymeric film 362 and inner facing sheet 304 mix together to form a bond. The ultrasonic bonding process may be configured such that it generates a through passage 320 generally within the confines of the bond region 322 in order to provide for the passage of water vapor 118 and give breathability to the laminate 24. These bonding sites 316 may correspond to the boding sites 116 already present in the laminate 24 (which consists of outer facing nonwoven sheet 358 and polymeric film 362). Alternatively, the bonding sites 316 may be not align to the existing bond sites 116 such that the bonding sites 316 create new through passages 320 that pass through the three layers of the laminate. In some embodiments, this will result in previous bond sites 116 that are covered on the inside by the inner facing nonwoven layer 304. The inner facing layer 304 may be a breathable nonwoven material such that water vapor 118 may pass through previous bond sites 116 even though those bond sites are now covered by the inner facing layer 304.

Referring again to FIG. 7, the front section 30 may have a second adhered portion 107 in which the covering nonwoven 104 is attached to the film laminate 24 by an adhesive or lamination process. The rear section 32 may have a corresponding adhered portion 111.

Figure 10:
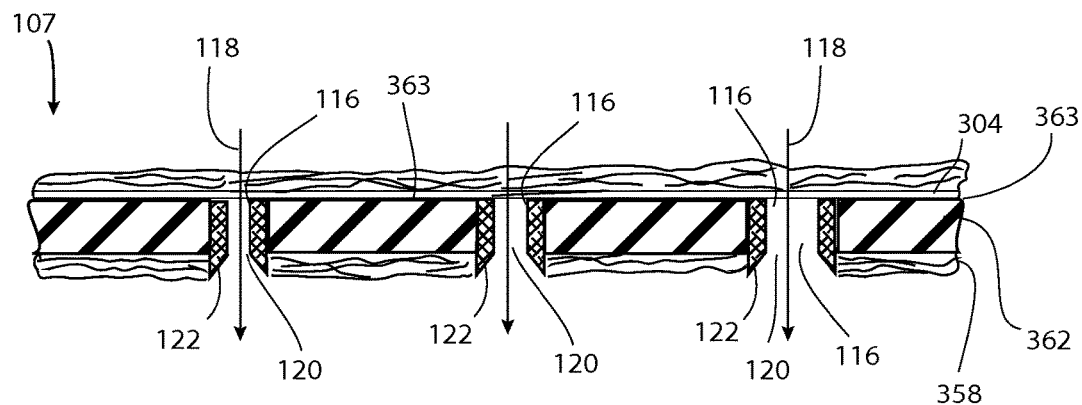
FIG. 10 is a cross-sectional view of an embodiment of a laminate used in a further portion of the absorbent article illustrated in FIG. 7.

As shown in FIG. 10, the covering nonwoven 304 may be attached to the polymeric layer 362 by application of an adhesive material 363. This adhesive may in a manner, such that it does not block some or all of the existing through passages 120. For example, the adhesive may be applied in a pattern such that it is applied to some of the through passages 120, but not others. Alternatively, the adhesive may be of a type or applied in such a manner that it does not fill or seal the existing through passages 120. Accordingly, provided that the inner facing layer 304 is a breathable material, water vapor 118 may pass through previous bond sites 116 even though those bond sites are now covered by the inner facing layer 304, and the breathability of these areas 107, 111 will be preserved.

The differently adhered areas 105, 107 of the front section 30 may be separated by a line 332 that runs transversely across the width of the absorbent article such that the upper waist area of the article fall generally within the first area 105 while the lower waist area and leg elastics 84, 86 fall generally within the second area 107. Alternatively, the differently adhered areas may be separated by a line 334 that more closely follows the contours of the leg elastics such that more of the waist area falls within the first area 105. Likewise, the differently adhered areas 109, 111 of the rear section 32 may be separated by a generally straight transverse line 336 or a more contoured line 338. It should be understood that the line separating these sections can be positioned and contoured as would be understood by one of skill in the art in order to performance, cost and other attributes of the absorbent article.

Figure 11:
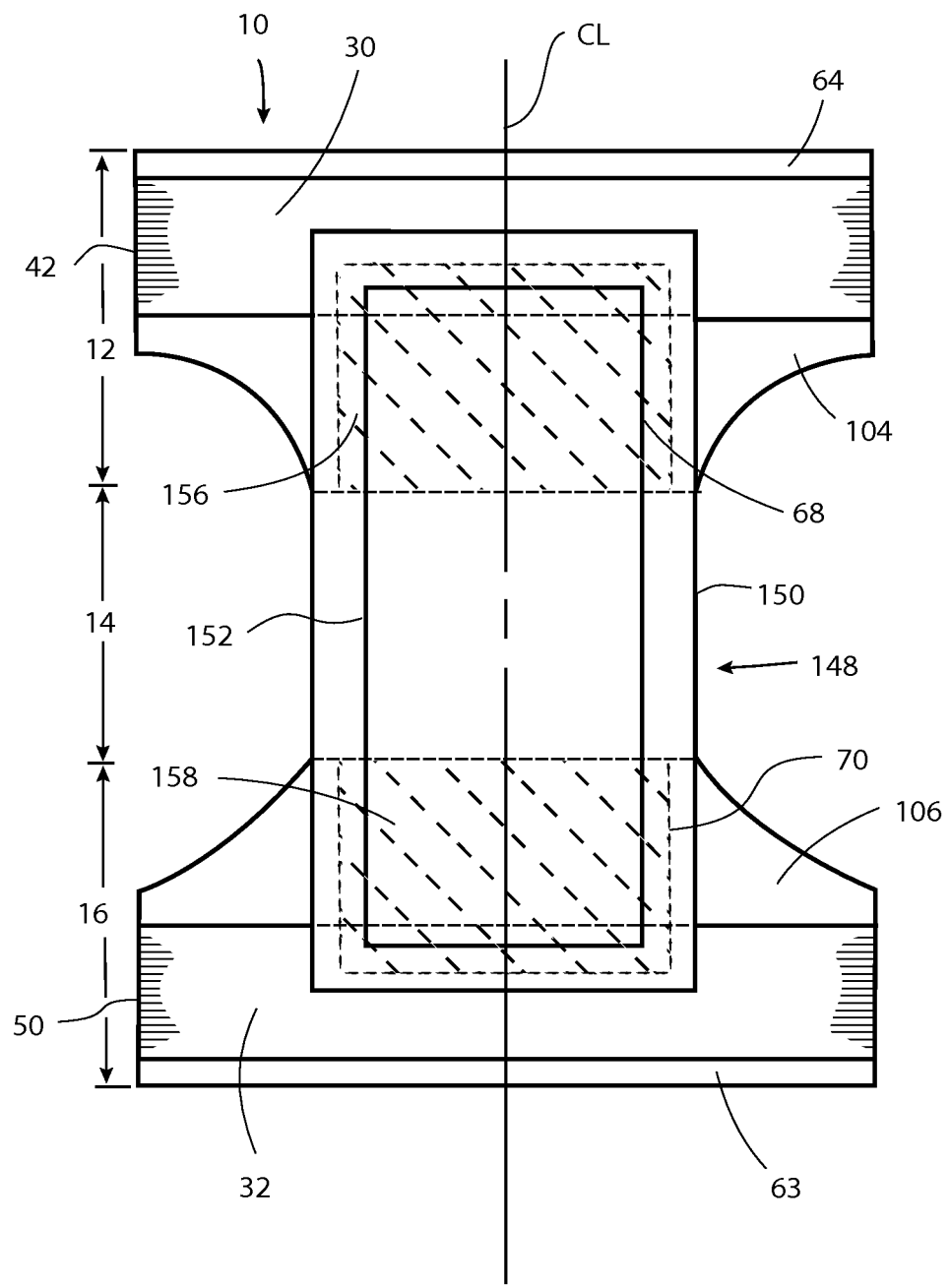
FIG. 11 is a top plan view of an embodiment of the absorbent article of FIG. 1 in a substantially flat un-contracted position and further including an absorbent assembly.
Figure 12:
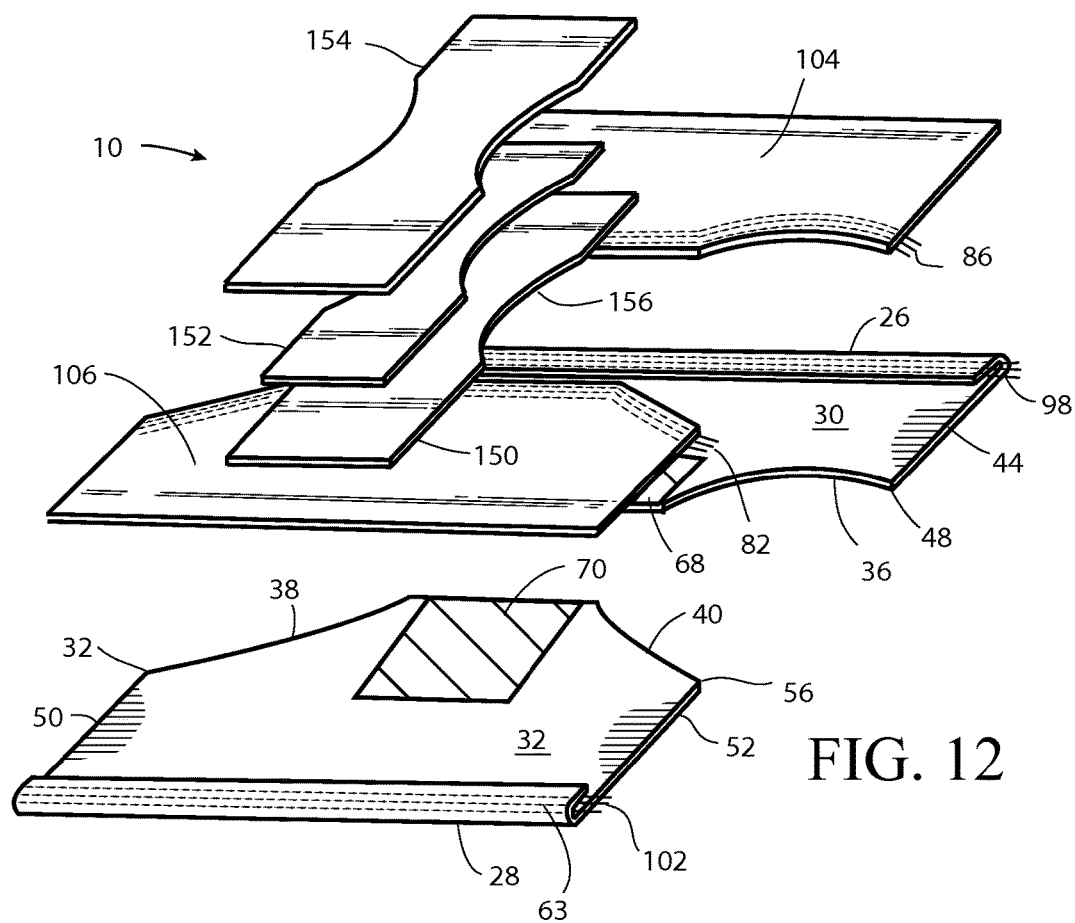
FIG. 12 is an exploded perspective view of an embodiment of the absorbent article of FIG. 11.

As illustrated in FIGS. 11-12, the absorbent article 10 also includes an absorbent assembly 148 that extends from the front section 12, across the crotch section 14, to the rear section 16. The absorbent assembly includes an absorbent core 152, and may include a topsheet 154 and a backsheet 150. (The topsheet 154 has been removed in FIG. 11 to more clearly show the position of the backsheet 150 and absorbent core 152.) The absorbent assembly 148 may be generally rectangular as shown in FIG. 11 or may comprise curved sections 166 to accommodate the wearer's legs as shown in FIG. 12. The absorbent core 152 may have an area that is smaller than the topsheet 154 and backsheet 150 such that the absorbent core is contained within the periphery of the absorbent assembly. The topsheet 154 and backsheet 150 may be bonded or otherwise adhered around a periphery of the absorbent assembly in order to capture the absorbent core 152 between the two sheets.

As shown in FIG. 11, the absorbent assembly 148 overlaps with the front section 30 to form a front overlapping zone 156, and the absorbent assembly 148 overlaps with the rear section 32 to form a rear overlapping zone 158. The periphery of the absorbent core 152 may be positioned completely within the front non-elastic portion 68 where the core overlaps with the front film section 30 and positioned completely within the rear non-elastic portion 70 where the core overlaps with the front film section 32. The backsheet 150 and topsheet (not shown) may also be positioned within the non-elastic portions 68, 70 in the overlapping zones, or may extend beyond the non-elastic portions as illustrated in FIG. 11.

In embodiments of the invention, the non-elastic portions 68, 70 may encompass more than 50% of the respective overlapping zones 156, 158. In other embodiments, more than 75%, and in further embodiments more than 90% of the area of the overlapping zones 156, 158 are non-elastomeric. In further embodiments, the entire of the overlapping zones are non-elastomeric. By adjusting the size of the non-elastic portions 68, 70 relative to the size of the absorbent core 152, the fit range of the article may be adjusted or the shape of the absorbent assembly may be defined in order to more readily capture exudate or prevent leaks.

In further embodiments, the non-elastic portions 68, 70 extend beyond the periphery of the absorbent core 152 or even beyond the backsheet 150. For example, non-elastic regions may be at least 10% larger, 20% larger, or in further embodiments 25% larger in area than the respective overlapped regions 156, 158. Providing non-elastic portions that are larger than their respective overlapping zones allows the process to accommodate any registration variability that may be present in the manufacturing process.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. Each of these embodiments and obvious variations thereof is contemplated as falling within the spirit and scope of the invention.

What is claimed is:

1. An absorbent article, comprising:
   a front laminate section defining a front end edge, a front crotch edge parallel to and longitudinally spaced from the front end edge, and first and second transversely opposed side edges extending in a longitudinal directions, the front laminate section comprising a front non-elastic portion adjacent to the front crotch edge, a front elastic portion adjacent to the front end edge, the front laminate section further comprising:
      a non-breathable polymeric film,
      a first nonwoven layer,
      a plurality of spaced apart ultrasonic bonding sites attaching the first nonwoven layer to a first side of the polymeric film,
      a plurality of breathable apertures through the polymeric film, wherein the plurality of breathable apertures consists of a series of through passages that provide for the passage of water vapor through the front laminate with each through passage being formed in conjunction with one of the plurality of ultrasonic bonding sites, and
      a second nonwoven layer attached to a second side of the polymeric film opposite the first nonwoven layer, wherein the second nonwoven layer is attached to the polymeric film by a first adherence mechanism in a first zone and a second adherence mechanism, different from the first adherence mechanism, in a second zone;
   a rear laminate section defining rear end edge, a rear crotch edge parallel to and longitudinally spaced from the rear end edge, and first and second transversely opposed side edges extending in a longitudinal directions, the rear laminate section comprising a rear non-elastic portion adjacent to the rear crotch edge and a rear elastic portion adjacent to the rear end edge; and
   an absorbent assembly extending longitudinally between the front crotch edge and the rear crotch edge, the absorbent assembly comprising a topsheet, a back sheet and an absorbent core positioned between the topsheet and backsheet.

2. The absorbent article of claim 1 wherein the absorbent assembly overlaps with the front non-elastic portion and the rear non-elastic portion and does not overlap with the front elastic portion and the rear elastic portion.

3. The absorbent article of claim 1 wherein the front laminate section farther defines a first leg edge, and the absorbent article further comprises:

a first leg elastic that is adhered to a surface of the front laminate section and extends parallel and adjacent to the leg edge from the side edge to an edge of the front non-elastic portion;

and a second leg elastic that is adhered to a surface of the front laminate section and that is increasingly separated in distance from first leg elastic as the leg elastics extend from the side edge to an edge of the front non-elastic portion.

4. The absorbent article of claim 3 wherein the leg elastic is positioned between the polymeric film and the second nonwoven layer.

5. The absorbent article of claim 1 wherein the polymeric film is an elastomeric film.

6. The absorbent article of claim 5 wherein the non-elastic portion of the front laminate is formed by deactivating a portion of the elastomeric film.

7. The absorbent article of claim 1 wherein the first adherence mechanism comprises a plurality of spaced apart bonding sites.

8. The absorbent article of claim 7 wherein the bonding sites are ultrasonic bonds.

9. The absorbent article of claim 1 wherein the second adherence mechanism comprises an adhesive material.

10. The absorbent article of claim 9 wherein the leg elastics are positioned within the second zone.

11. An absorbent article, comprising:
a breathable front laminate section defining front end edge, a front crotch edge parallel to and longitudinally spaced from the front end edge, first and second transversely opposed side edges extending in a longitudinal directions, and first and second leg edges, the front laminate section comprising:
a non-breathable polymeric film,
a first nonwoven layer attached to a first side of the polymeric film at a plurality of spaced apart bonding sites,
a second nonwoven layer attached to a second side of the polymeric film opposite the first nonwoven layer, wherein the second nonwoven layer is attached to the polymeric film by a first adherence mechanism in a first zone and a second adherence mechanism different from the first adherence mechanism, in a second zone,
a front non-elastic portion adjacent to the front crotch edge, and
a front elastic portion adjacent to the front end edge, and
a plurality of breathable apertures through the polymeric film, wherein the plurality of breathable apertures consists of a series of through passages that provide for the passage of water vapor through the front laminate with each through passage being formed in conjunction with one of the plurality of bonding sites;
a rear laminate section defining rear end edge, a rear crotch edge parallel to and longitudinally spaced from the rear end edge, first and second transversely opposed side edges extending in a longitudinal directions, and first and second leg edges, the rear laminate section comprising a rear non-elastic portion adjacent to the rear crotch edge and a rear elastic portion adjacent to the rear end edge; and
an absorbent assembly extending longitudinally between the front crotch edge and the rear crotch edge, the absorbent assembly comprising a topsheet, a back sheet and an absorbent core positioned between the topsheet and backsheet.

12. The absorbent article of claim 11 wherein the bonding sites are ultrasonic bonding sites.

13. The absorbent article of claim 12 wherein the through passages are formed within a perimeter of the ultrasonic bonding site.

14. The absorbent article of claim 12 wherein the through passages are tears formed in the polymeric film with each tear being outside of and adjacent to a perimeter of the ultrasonic bonding site.

15. The absorbent article of claim 11 wherein the front laminate section further defines a first leg edge, and the absorbent article further comprises:
a first leg elastic that is adhered to a surface of the front laminate section and extends parallel and adjacent to the leg edge from the side edge to an edge of the front non-elastic portion;
and a second leg elastic that is adhered to a surface of the front laminate section and that is increasingly separated in distance from first leg elastic as the leg elastics extend from the side edge to an edge of the front non-elastic portion.

16. The absorbent article of claim 1 wherein the through passages are formed within a perimeter of the ultrasonic bonding site.

17. The absorbent article of claim 1 wherein the through passages are tears formed in the polymeric film with each tear being outside of and adjacent to a perimeter of the ultrasonic bonding site.

* * * * *